US008062677B2

(12) United States Patent
Komorowski

(10) Patent No.: US 8,062,677 B2
(45) Date of Patent: Nov. 22, 2011

(54) METHODS AND COMPOSITIONS FOR THE SUSTAINED RELEASE OF CHROMIUM

(75) Inventor: James R. Komorowski, Trumbell, CT (US)

(73) Assignee: Nutrition 21, Inc., Purchase, NY (US)

( * ) Notice: Subject to any disclaimer, the term of this patent is extended or adjusted under 35 U.S.C. 154(b) by 221 days.

(21) Appl. No.: 12/340,257

(22) Filed: Dec. 19, 2008

(65) Prior Publication Data

US 2009/0155384 A1   Jun. 18, 2009

Related U.S. Application Data

(63) Continuation of application No. PCT/US2008/056545, filed on Mar. 11, 2008.

(60) Provisional application No. 60/894,601, filed on Mar. 13, 2007.

(51) Int. Cl.
*A01N 59/16* (2006.01)
*A01N 55/02* (2006.01)
*A61K 31/28* (2006.01)
*A61K 33/24* (2006.01)
*A61K 31/555* (2006.01)

(52) U.S. Cl. ......... 424/655; 514/184; 514/188; 514/505

(58) Field of Classification Search ........................ None
See application file for complete search history.

(56) References Cited

U.S. PATENT DOCUMENTS

| 5,164,384 | A | 11/1992 | Paul | |
|---|---|---|---|---|
| 6,251,889 | B1 * | 6/2001 | de la Harpe et al. | 514/188 |
| 2002/0081315 | A1 * | 6/2002 | Katz et al. | 424/195.16 |
| 2003/0211172 | A1 | 11/2003 | Jones et al. | |
| 2005/0069593 | A1 | 3/2005 | Zwiefel | |
| 2005/0233946 | A1 | 10/2005 | Fine et al. | |

FOREIGN PATENT DOCUMENTS

| WO | WO 00/12095 | 3/2000 |
|---|---|---|
| WO | WO 02/36127 | 5/2002 |
| WO | WO 02/36202 | 5/2002 |
| WO | WO 02/067953 | 9/2002 |
| WO | WO 03/043569 | 5/2003 |
| WO | WO 03/090671 | 11/2003 |

OTHER PUBLICATIONS

Anderson et al., (Biol Trace Elem Research. 2004;101:211-218).*
EP Extended Search Report, dated May 7, 2005, PCT/US2008/056545.
International Search Report and Written Opinion, dated Jul. 31, 2008, PCT/US2008/056545.
International Preliminary Report on Patentability, dated Mar. 13, 2007, PCT/US2008/056545.

* cited by examiner

*Primary Examiner* — Cherie M Woodward
(74) *Attorney, Agent, or Firm* — Knobbe Martens Olson & Bear LLP

(57) ABSTRACT

Provided herein are compositions for the administration of chromium that include at least two components: a hydrophilic chromium complex and a lipophilic chromium complex, and methods of using the same. Also provided are compositions for the administration of chromium that include a first "fast-acting" chromium complex and a second "slow-acting" chromium complex, wherein the first chromium complex is absorbed more quickly than the slow-acting chromium complex, and methods of using the same. Also provided herein are methods for treating, preventing, and improving conditions associated with cardiometabolic syndrome, by identifying a subject in need of treatment, prevention, or improvement of a condition associated with cardiometabolic syndrome, and providing a therapeutically effective amount of a composition comprising a fast-acting chromium complex and a slow-acting chromium complex, to the individual.

5 Claims, 5 Drawing Sheets

A

B

A. Normal Rats - Triglycerides

B. HFD Rats - Triglycerides

METHODS AND COMPOSITIONS FOR THE SUSTAINED RELEASE OF CHROMIUM

RELATED APPLICATIONS

The present application is a continuation of PCT/US2008/056545, filed Mar. 11, 2008, which designated the United States and was published in English, which claims priority under 35 U.S.C. §119(a)-(d) to U.S. Provisional Application Ser. No. 60/894,601, filed on Mar. 13, 2007, by Komorowski et al., entitled "COMBINATIONS OF CHROMIUM HISTIDINATE AND CHROMIUM." The content of each of these applications is hereby incorporated by reference in its entirety.

BACKGROUND OF THE INVENTION

1. Field of the Invention

Embodiments disclosed herein relate to compositions that comprise, consist essentially of, or consist of a hydrophilic chromium complex and a lipophilic chromium complex, and uses thereof, as well as compositions that comprise, consist essentially of, or consist of a first and a second chromium complex, wherein the first chromium complex is absorbed more quickly than the second chromium complex, and uses thereof. Other embodiments disclosed herein relate to the use of compositions comprising, consisting essentially of, or consisting of chromium and histidine, chromium histidinate complex, chromium trihistidinate, chromium polyhistidinate complex, chromium acetate, chromium chloride, or chromium nicotinate or combinations thereof, including pharmaceutically acceptable salts, hydrates, solvates, or mixtures thereof in combination with another chromium complex for sustained release of chromium. These compositions are useful in ameliorating a variety of conditions including cardiometabolic syndrome and related conditions, diseases, and disorders, improving glucose tolerance and glucose metabolism, treatment of insulin resistance, reducing pre-prandial and post-prandial glucose levels, reducing hyperglycemia and stabilizing serum glucose, reducing free fatty acids, reducing cortisol levels, improvement in lipid profiles, and promoting weight loss.

2. Description of the Related Art

Cardiometabolic Syndrome

Cardiometabolic syndrome (CMS) describes a constellation of maladaptive cardiovascular, renal, metabolic, prothrombotic, and inflammatory abnormalities. CMS is recognized as a disease entity by the American Society of Endocrinology, National Cholesterol Education Program, and World Health Organization, and is characterized by various salient features such as obesity, hypertension, dyslipidemia, impaired glucose tolerance, increase in inflammatory markers such as C-reactive protein (CRP), cytokines, tumor necrosis factor alpha (TNFα), interleukins 6 and 10 (IL-6 and IL-10), changes in cell adhesion molecules, prothrombotic and fibrinolytic changes, increase in oxidative stress and endothelial dysfunction. Juturu, 2006 *DPG Medical Nutrition Therapy*. Several of the conditions associated with CMS, e.g. obesity, hyperlipidemia, and diabetes, play a causal role in atherosclerotic cardiovascular diseases, which currently account for a considerable proportion of mortality and morbidity in developed, developing and underdeveloped societies.

Atherosclerosis

Atherosclerosis is a slowly progressive disease characterized by the accumulation of cholesterol within the arterial wall. Without wishing to be bound by any particular theory and solely for the purposes of expanding knowledge in the field, it is thought that lipids deposited in atherosclerotic lesions are derived primarily from plasma apolipoprotein B (apo B)-containing lipoproteins, which include chylomicrons, very low density lipoproteins (VLDL), intermediate-density lipoproteins (IDL), and LDL. Apo B-containing lipoproteins, and in particular LDL, are associated with adverse health outcomes. By contrast, HDL serum levels correlate inversely with coronary heart disease. Indeed, high serum levels of HDL are regarded as a negative risk factor for CHD, and studies suggest that high levels of plasma HDL are not only protective against coronary artery disease, but may actually induce regression of atherosclerotic plaque. See, e.g. Badimon et al., 1992 *Circulation* 86:(Suppl. III) 86 94; Dansky and Fisher, 1999, *Circulation* 100:1762 3. Data also suggest that non-HDL cholesterol (non HDL-C) might be a better predictive risk factor of CVD than LDL-C. The Adult Treatment Panel (ATP-III) recommended using non-HDL-C in assessing CVD risk in patients with Type II Diabetes Mellitus.

Cholesterol

As discussed above, elevated serum cholesterol is linked to coronary heart disease. Circulating cholesterol is carried by plasma lipoproteins, which are particles of complex lipid and protein composition that transport lipids in the blood. Low density lipoprotein (LDL) and high density lipoprotein (HDL) are the major cholesterol-carrier proteins. LDL is believed to be responsible for the delivery of cholesterol from the liver, where it is synthesized or obtained from dietary sources, to extrahepatic tissues in the body. "Reverse cholesterol transport" refers to the transport of cholesterol from extrahepatic tissues to the liver, where it is catabolized and eliminated. It is believed that plasma HDL particles play a major role in the reverse transport process, acting as scavengers of tissue cholesterol. HDL is also responsible for the removal of non-cholesterol lipid, oxidized cholesterol and other oxidized products from the bloodstream. The atherogenic index of plasma (AIP), defined as logarithm [log] of the ratio of plasma concentration of triglycerides (TG) to HDL-cholesterol (TG/HDL-C), has recently been proposed as a predictive marker for plasma atherogenicity and is positively correlated with cardiovascular disease (CVD). Lipoprotein subclass abnormalities that accompany insulin resistance are characterized by large, triglyceride-enriched very low-density lipoprotein (VLDL) particles; small, cholesterol-depleted LDL particles; and small HDL particles. In addition, more severe states of insulin resistance have been associated with progressively higher numbers of VLDL particles, intermediate-density lipoprotein particles and, most importantly, LDL particles. The strong correlation of atherogenic index in plasma with lipoprotein particle size may explain its association with cardiovascular disease (CVD) risk. Atherogenic dyslipidemia results in increased atherosclerotic plaque formation because of an imbalance between an increased number of small, dense LDL particles, which carry cholesterol to the vascular endothelium, and a decreased number of HDL particles, which remove cholesterol from atherosclerotic vessels. Insulin resistance is the initial physiological defect in the pathogenesis of diabetes, such as Type II diabetes mellitus ("T2DM"); the associated atherogenic lipoprotein phenotype considerably enhances the risk of CVD. The combination of these factors may lead to cardiometabolic syndrome which is different from metabolic syndrome. Hyperinsulinemia is often clustered with other cardiovascular risk factors; the presence of endogenous hyperinsulinemia combined with hypertriglyceridemia (HTG), increased body mass index, and a decreased HDL-C increase the risk of CHD death in patients with T2DM. Castro et al, 2003, *Curr Hypertens Rep.* 5(5): 393-401; Lastra et al. 2006, *Curr Diab Rep.* 6(3):207-12.

Cholesterol Transport

The fat-transport system can be divided into two pathways: an exogenous one for cholesterol and triglycerides absorbed from the intestine and an endogenous one for cholesterol and triglycerides entering the bloodstream from the liver and other non-hepatic tissue.

In the exogenous pathway, dietary fats are packaged into lipoprotein particles called chylomicrons, which enter the bloodstream and deliver their triglycerides to adipose tissue for storage and to muscle for oxidation to supply energy. The remnant of the chylomicron, which contains cholesteryl esters, is removed from the circulation by a specific receptor found only on liver cells. This cholesterol then becomes available again for cellular metabolism or for recycling to extrahepatic tissues as plasma lipoproteins.

In the endogenous pathway, the liver secretes a large, very-low-density lipoprotein particle (VLDL) into the bloodstream. The core of VLDL consists mostly of triglycerides synthesized in the liver, with a smaller amount of cholesteryl esters either synthesized in the liver or recycled from chylomicrons. Two predominant proteins are displayed on the surface of VLDL, apolipoprotein B-100 (apo B-100) and apolipoprotein E (apo E), although other apolipoproteins are present, such as apolipoprotein CIII (apo CIII) and apolipoprotein CII (apo CII). When VLDL reaches the capillaries of adipose tissue or of muscle, its triglyceride is extracted. This results in the formation of a new kind of particle called intermediate-density lipoprotein (IDL) or VLDL remnant, decreased in size and enriched in cholesteryl esters relative to a VLDL, but retaining its two apoproteins.

In human beings, about half of the IDL particles are removed from the circulation quickly, generally within two to six hours of their formation. This is because IDL particles bind tightly to liver cells, which extract IDL cholesterol to make new VLDL and bile acids. The IDL not taken up by the liver is catabolized by the hepatic lipase, an enzyme bound to the proteoglycan on liver cells. Apo E dissociates from IDL as it is transformed to LDL. Apo B-100 is the sole protein of LDL.

Primarily, the liver takes up and degrades circulating cholesterol to bile acids, which are the end products of cholesterol metabolism. The uptake of cholesterol-containing particles is mediated by LDL receptors, which are present in high concentrations on hepatocytes. The LDL receptor binds both apo E and apo B-100 and is responsible for binding and removing both IDL and LDL from the circulation. In addition, remnant receptors are responsible for clearing chylomicrons and VLDL remnants, i.e., IDL. However, the affinity of apo E for the LDL receptor is greater than that of apo B-100. As a result, the LDL particles have a much longer circulating life span than IDL particles; LDL circulates for an average of two and a half days before binding to the LDL receptors in the liver and other tissues. High serum levels of LDL are positively associated with coronary heart disease. For example, in atherosclerosis, cholesterol derived from circulating LDL accumulates in the walls of arteries. This accumulation forms bulky plaques that inhibit the flow of blood until a clot eventually forms, obstructing an artery which may ultimately lead to heart attack or stroke.

Ultimately, the amount of intracellular cholesterol liberated from the LDL controls cellular cholesterol metabolism. The accumulation of cellular cholesterol derived from VLDL and LDL controls three processes. First, it reduces the ability of the cell to make its own cholesterol by turning off the synthesis of HMGCoA reductase, a key enzyme in the cholesterol biosynthetic pathway. Second, the incoming LDL-derived cholesterol promotes storage of cholesterol by the action of cholesterol acyltransferase ("ACAT"), the cellular enzyme that converts cholesterol into cholesteryl esters that are deposited in storage droplets. Third, the accumulation of cholesterol within the cell drives a feedback mechanism that inhibits cellular synthesis of new LDL receptors. Cells, therefore, adjust their complement of LDL receptors so that enough cholesterol is brought in to meet their metabolic needs, without overloading.

High levels of apo B-containing lipoproteins can be trapped in the subendothelial space of an artery and undergo oxidation. The oxidized lipoprotein is recognized by scavenger receptors on macrophages. Binding of oxidized lipoprotein to the scavenger receptors can enrich the macrophages with cholesterol and cholesteryl esters independently of the LDL receptor. Macrophages can also produce cholesteryl esters by the action of ACAT. LDL can also be complexed to a high molecular weight glycoprotein called apolipoprotein (a), also known as apo(a), through a disulfide bridge. The LDL-apo(a) complex is known as Lipoprotein(a) or Lp(a). Elevated levels of Lp(a) are detrimental, having been associated with atherosclerosis, coronary heart disease, myocardial infarction, stroke, cerebral infarction, and restenosis following angioplasty. Wang et al. 2006, *J Lipid Res.* 5.

Reverse Cholesterol Transport

Peripheral (non-hepatic) cells predominantly obtain their cholesterol from a combination of local synthesis and uptake of preformed sterol from VLDL and LDL. Cells expressing scavenger receptors, such as macrophages and smooth muscle cells, can also obtain cholesterol from oxidized apo B-containing lipoproteins. In contrast, reverse cholesterol transport (RCT) is the pathway by which peripheral cell cholesterol can be returned to the liver for recycling to extrahepatic tissues, hepatic storage, or excretion into the intestine in bile. The RCT pathway represents the only means of eliminating cholesterol from most extrahepatic tissues and is crucial to the maintenance of the structure and function of most cells in the body.

The enzyme in blood involved in the RCT pathway, lecithin:cholesterol acyltransferase (LCAT), converts cell-derived cholesterol to cholesteryl esters, which are sequestered in HDL destined for removal. LCAT is produced mainly in the liver and circulates in plasma associated with the HDL fraction. Cholesterol ester transfer protein (CETP) and another lipid transfer protein, phospholipid transfer protein (PLTP), contribute to further remodeling the circulating HDL population. PLTP supplies lecithin to HDL, and CETP can move cholesteryl esters made by LCAT to other lipoproteins, particularly apoB-containing lipoproteins, such as VLDL. HDL triglycerides can be catabolized by the extracellular hepatic triglyceride lipase and lipoprotein cholesterol is removed by the liver via several mechanisms.

Each HDL particle contains at least one molecule, and usually two to four molecules, of apolipoprotein A I (apo A I). Apo A I is synthesized by the liver and small intestine as preproapolipoprotein, which is secreted as a proprotein that is rapidly cleaved to generate a mature polypeptide having 243 amino acid residues. Apo A I consists mainly of a 22 amino acid repeating segment, spaced with helix-breaking proline residues. Apo A I forms three types of stable structures with lipids: small, lipid-poor complexes referred to as pre-beta-1 HDL; flattened discoidal particles, referred to as pre-beta-2 HDL, which contain only polar lipids (e.g., phospholipid and cholesterol); and spherical particles containing both polar and nonpolar lipids, referred to as spherical or mature HDL (HDL3 and HDL2). Most HDL in the circulating population contains both apo A I and apo A II, a second major HDL protein. The apo A I- and apo A II-containing fraction is referred to herein as the AI/AII-HDL fraction of HDL. The fraction of HDL containing only apo A I, referred to herein as the AI HDL fraction, appears to be more effective in RCT. Certain epidemiologic studies support the hypothesis that the AI-HDL fraction is antiartherogenic. Spady et al. 1999, *Circulation*. 100:576-578; Fielding C J, Fielding P E. 1995, *J Lipid Res*. 36:211-228.

The LCAT reaction requires an apolipoprotein such as apo A I or apo A-IV as an activator. ApoA-I is one of the natural cofactors for LCAT. The conversion of cholesterol to its HDL-sequestered ester prevents re-entry of cholesterol into the cell, resulting in the ultimate removal of cellular cholesterol.

HDL is not only involved in the reverse transport of cholesterol, but also plays a role in the reverse transport of other lipids, e.g. the transport of lipids from cells, organs, and tissues to the liver for catabolism and excretion. Such lipids include sphingomyelin, oxidized lipids, and lysophophatidylcholine. For example, Robins and Fasulo have shown that HDL stimulates the transport of plant sterol by the liver into bile secretions. Robins and Fasulo (1997, *J. Clin. Invest.* 99:380 384.

Cardiometabolic Syndrome

Available data suggest that insulin resistance is responsible for more than 40% of heart attacks and is the underlying cause for various risk factors, which lead to cardiometabolic syndrome (CMS).

In cardiovascular tissues there are two pathways of insulin receptor signaling: one that is predominant in metabolic tissues (mediated by phosphatidylinositol-3-kinase); and a growth factor-like pathway (mediated by MAPK). The first pathway can lead to atherosclerosis. Patients presenting with multiple cardiometabolic risk factors have triple the risk of experiencing a myocardial infarction and/or stroke and double the risk of mortality. In addition, the risk for developing type 2 diabetes, if not already present, is fivefold above the risk in patients without CMS.

In addition to the risks discussed above, hyperinsulinemia and hypertension, two conditions associated with CMS, can also contribute significantly to progressive renal disease. Other mechanisms that potentially lead to progressive renal disease and CMS can include endothelial dysfunction, left ventricular hypertrophy (LVH), cardiac hyperreactivity, dyslipidemia, hyperglycemia, enhanced renin-angiotensin-aldosterone system (RAAS) activity, altered renal structure and function with impaired pressure natriuresis leading to sodium retention, volume expansion, progressive renal disease, and eventually end-stage renal disease (ESRD).

It has also been suggested that the impact of the CMS is largely independent from glycaemic control, and is associated with several neglected modifiable and non modifable risk factors, such as abdominal obesity, especially visceral obesity. A common pathophysiologic process, such as endothelial dysfunction, chronic low-grade inflammation, or increased transvascular leakage of macromolecules, can underlie the association between microalbuminuria and cardiovascular disease. Microalbuminuria has been implicated as an independent risk factor for CVD and premature cardiovascular mortality for patients with type 1 and type 2 diabetes mellitus, as well as for patients with essential hypertension. The combination of diabetes and CHD risk factors could be explained by metabolic abnormalities that are not currently assessed in daily clinical practice. It is therefore suggested that in order to optimally manage these risk factors, attention should be given not only to reduce risk factors, but also to the improvement of features of the CMS Juturu, 2006 *DPGMNT*.

Insulin resistance is a condition that is characterized by decreased insulin function and hyperinsulinemia. Individuals who have insulin resistance also have an increased risk of developing diabetes mellitus, dyslipidemia, hypertension, atherosclerosis, endothelial dysfunction, microalbuminuria, obesity, depression, Syndrome X, and polycystic ovary syndrome, among other conditions. In addition, all of the aforementioned conditions carry the risk of developing associated diseases. For example, diabetes increases the risk of developing associated diseases such as diabetic nephropathy, neuropathy, and retinopathy.

Insulin resistance may result from taking certain drug therapies such as statins, non-steroidal anti-inflammatory drugs (NSAIDS), steroids, oral contraceptives, hormone replacement therapy (HRT), beta blockers, potassium channel openers, diuretics, immunosuppressive drugs, etc. For example, A. Jula et al. report that fasting serum insulin levels increased 13% and insulin resistance increased by 14% in 120 nondiabetic hypercholesterolemic male patients taking statin drugs to reduce their cholesterol levels. A. Jula et al., 2002, *JAMA* 287:598-605, 604. Furthermore, it has also been reported that beta blockers and diuretics worsen insulin resistance and that patients taking beta blockers had a 28% higher incidence of diabetes than untreated patients with hypertension. S. Julius et al., 2001, *Am. J. Hypertens.* 14:310 S-316S, 313S.

Insulin resistance has also been described as a side effect of a variety of oral contraceptives. In a study of the metabolic effects of implantable steroid contraceptives, altered glucose tolerance characterized by decreased insulin sensitivity following glucose administration was seen in individuals with implantable contraceptives, such as NORPLANT®, JADELLE®, and IMPLANON® was observed. Dorfgliner, L. J., 2002, *Contraception* 65:47-62, Peterson, K. R., 2002, *Danish Medical Bulletin* 49:43-60. Similarly, oral contraceptives and hormone replacement therapy ("HRT") have been linked to the onset of microalbuminuria. Monster, T. B. M et al., 2001, *Arch Intern Med.* 161:2000-2005.

Often, physicians will prescribe a hypoglycemic drug such as metformin, which the patient must continue to take for the rest of the patient's life, for individuals presenting with insulin resistance.

The Role of Chromium

Dietary supplementation of chromium to normal individuals has been reported to lead to improvements in glucose tolerance, serum lipid concentrations, including high-density lipoprotein cholesterol, insulin and insulin binding. Anderson, 1986 *Clin. Psychol. Biochem.* 4:31-41. Supplemental chromium in the trivalent form, e.g. chromic chloride, is associated with improvements of risk factors associated with adult-onset (Type 2) diabetes and cardiovascular disease.

Chromium is a nutritionally essential trace element. The necessity of dietary chromium was established in 1959 by Schwartz. Schwartz, "Present Knowledge in Nutrition," page 571, fifth edition (1984, the Nutrition Foundation, Washington, D.C.). Chromium depletion is characterized by the disturbance of glucose, lipid and protein metabolism and by a shortened lifespan. Chromium is essential for optimal insulin activity in all known insulin-dependent systems. Boyle et al., 1977 *Southern Med. J.* 70:1449-1453. Insufficient dietary chromium has been linked to both maturity-onset diabetes and to cardiovascular disease.

The principal energy sources for the body are glucose and fatty acids. Chromium depletion results in biologically ineffective insulin and compromised glucose metabolism. Under these conditions, the body relies primarily upon lipid metabolism to meet its energy requirements, which can lead to the production of elevated amounts of acetyl-CoA and ketone bodies. In some cases, some of the acetyl-CoA can be diverted to increased cholesterol biosynthesis, resulting in hypercholesterolemia. As such, glycosuria, hypercholesterolemia, and often ketoacidosis are often associated with diabetes mellitus. The accelerated atherosclerotic process seen in diabetics is associated with hypercholesterolemia Boyle et al., supra.

Chromium functions as a cofactor for insulin. It binds to the insulin receptor and potentiates many, and perhaps all, of its functions. Boyle et al., supra. These functions include, but are not limited to, the regulation of carbohydrate and lipid metabolism. Present Knowledge in Nutrition, supra, at p. 573-577. The introduction of inorganic chromium compounds per se into individuals is not particularly beneficial. Chromium must be converted endogenously into an organic complex or must be consumed as a biologically active molecule. Only about 0.5% of ingested inorganic chromium, however, is assimilated into the body. Only 1-2% of most organic chromium compounds are assimilated into the body. Recommended Daily Allowances, Ninth Revised Edition, The National Academy of Sciences, page 160, 1980.

U.S. Pat. No. Re. 33,988 discloses that when selected essential metals, including chromium, are administered to mammals as exogenously synthesized coordination complexes of picolinic acid, they are directly available for absorption without competition from other metals. U.S. Pat. No. Re. 33,988 describes a composition and method for selectively supplementing the essential metals in the human diet and for facilitating absorption of these metals by intestinal cells. These complexes are safe, inexpensive, biocompatible, and easy to produce. These exogenously synthesized essential metal coordination complexes of picolinic acid (pyridine-2-carboxylic acid) have the following structural formula:

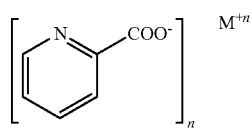

wherein M represents the metallic cation and n is equal to the cation's valence. For example, when M is Cr and n=3, then the compound is chromic tripicolinate. Other chromium picolinates disclosed include chromic monopicolinate and chromic dipicolinate.

The U.S. Recommended Daily Intake (RDI) of chromium is 120 µg. U.S. Pat. No. 5,087,623, the entire contents of which are hereby expressly incorporated herein by reference, describes the administration of chromic tripicolinate for the treatment of adult-onset diabetes in doses ranging from 50 to 500 µg. U.S. Pat. No. 6,329,361, the entire contents of which are hereby expressly incorporated herein by reference, discloses the use of high doses of chromic tripicolinate (providing 1,000-10,000 µg chromium/day) for reducing hyperglycemia and stabilizing the level of serum glucose in humans with Type 2 diabetes. U.S. Pat. Nos. 5,789,401 and 5,929,066, the entire contents of which are hereby expressly incorporated herein by reference, disclose a chromic tripicolinate-biotin composition and its use in lowering blood glucose levels in humans with Type 2 diabetes.

U.S. Pat. Nos. 5,087,623; 5,087,624; and 5,175,156, the entire contents of which are hereby expressly incorporated herein by reference, disclose the use of chromium tripicolinate for supplementing dietary chromium, reducing hyperglycemia and stabilizing serum glucose, increasing lean body mass and reducing body fat, and controlling serum lipid levels, including the lowering of undesirably high serum LDL-cholesterol levels and the raising of serum High Density Lipid (HDL)-cholesterol levels. U.S. patent application Ser. Nos. and 10/090,038 and 11/136,794, the entire contents of which are hereby expressly incorporated by reference in their entireties, disclose the use of high doses of chromium complexes (providing between 1,000 and 10,000 µg/day) and biotin for treating dyslipidemia, and increasing serum HDL levels.

U.S. Pat. Nos. 4,954,492 and 5,194,615, the entire contents of which are hereby expressly incorporated by reference, describe a related complex, chromic nicotinate, which is also used for supplementing dietary chromium and lowering serum lipid levels. Picolinic acid and nicotinic acid are position isomers having the following structures:

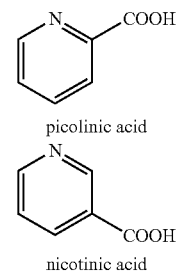

picolinic acid nicotinic acid

Nicotinic acid and picolinic acid form coordination complexes with monovalent, divalent and trivalent metal ions and facilitate the absorption of these metals by transporting them across intestinal cells and into the bloodstream.

Other compounds such as non-steroidal anti-inflammatory drugs (NSAIDs) such as aspirin and indomethachin have also been shown to facilitate chromium absorption. For Example, Davis et al. demonstrated that orally administered $CrCl_3$ is facilitated by the non-steroidal anti-inflammatory drugs (NSAIDs) aspirin and indomethacin. Davis et al., 1995, *Nutrition Res.* 15:202-210 (1995); Kamath et al., 1997, *J. Nutrition* 127:478-482. These drugs inhibit the enzyme cyclooxygenase which converts arachidonic acid to various prostaglandins, resulting in inhibition of intestinal mucus formation and lowering of intestinal pH which facilitates chromium absorption.

U.S. Pat. No. 4,315,927 teaches that when selected essential metals are administered to mammals as exogenously synthesized coordination complexes of picolinic acid, they are directly available for absorption without competition from other metals. These complexes are safe, inexpensive, biocompatible and easy to produce.

There remains a need for sources of chromium that exhibit favorable absorption profiles, and also that provide for the release of chromium from the coordination complex once within the cell. Further, there remains a need for compositions that provide sources of chromium with differing absorption profiles to provide a fast and slow-acting source of chromium.

SUMMARY OF THE INVENTION

Provided herein are improved compositions for supplementing chromium in individuals. Some embodiments provide compositions for the administration of chromium over a period of time. Such compositions can comprise, consist of, or consist essentially of a lipophilic chromium complex and a hydrophilic chromium complex, or a first chromium complex and a second chromium complex, wherein the first chromium complex is absorbed more quickly (fast-acting) than the second chromium complex (slow-acting). For example, in some embodiments, the lipophilic chromium complex or slow-acting chromium complex can be chromium picolinate or chromium tripicolinate, and the hydrophilic chromium complex or fast-acting chromium complex can be any one of chromium acetate, chromium chloride, chromium histidinate, and chromium nicotinate, or any combination thereof. In some embodiments, the hydrophilic chromium complex or fast-acting chromium complex is chromium histidinate. In some embodiments, the slow-acting or lipophilic chromium complex is chromium picolinate. In some embodiments, the compositions are pharmaceutical compositions comprising one or more compositions disclosed herein, with a pharmaceutically acceptable vehicle, excipient, or diluent. For example, pharmaceutically acceptable vehicles can include carriers, excipients, diluents, and the like, as well as combinations or mixtures thereof.

Also provided herein are methods of using the compositions described herein. For example, embodiments provide methods for reducing pre-prandial and post-prandial glucose levels, for reducing hyperglycemia or stabilizing serum glucose levels, for improving insulin sensitivity, for reducing free fatty acid levels, and for treating dyslipidemia by identifying a subject in need of a reduction in pre or post-prandial glucose levels, a reduction in hyperglycemia, a stabilization of serum glucose levels, and improvement in insulin sensitivity, a reduction in free fatty acid levels, or treatment for dyslipidemia, and providing a therapeutically effective amount of the compositions described above to said individual. In some embodiments, the therapeutically effective amount of the fast-acting and the slow-acting chromium complex provides a glucose lowering effect or glucose stabilization effect for at least 10 hours.

In certain embodiments of the methods described herein, the hydrophilic chromium complex and the lipophilic chromium complex, or the first chromium complex and the second chromium complex can be provided at substantially the same time, e.g. in a single composition. In other embodiments, the hydrophilic chromium complex and the lipophilic chromium complex, or the first chromium complex and the second chromium complex can be provided sequentially in either order.

Embodiments disclosed herein also relate to improved compositions for lowering serum glucose levels, for improving insulin sensitivity, for treating dyslipidemia, and for increasing lean muscle mass. The improved compositions can include synergistically effective amount of a hydrophilic and a lipophilic chromium complex, e.g. chromium histidinate and chromium picolinate, wherein the synergistically effective amount of chromium histidinate and said chromium picolinate have a greater than additive effect in lowering serum glucose levels, improving insulin sensitivity, treating dyslipidemia, and increasing lean muscle mass, respectively.

In some embodiments, the ratio of the lipophilic or slow-acting chromium complex to the hydrophilic or fast-acting chromium complex is about 0.0001:1, 0.001:1, 0.01:1, 0.1:1, 0.2:1; 0.3:1, 0.4:1; 0.5:1; 0.75:1, 1:1, 1:1.1, 1.2:1, 1.3:1, 1.4:1, 1.5:1, 1.75:1, 2:1, 5:1, 10:1, 100:1, 500:1, or any ratio in between.

Also provided herein are compositions comprising chromium and histidine, chromium histidinate, chromium histidinate complexes, and combinations thereof, e.g. chromium with histidinate or histidinate complex or poly histidinate or mono histidinate in combination with a lipophilic chromium complex, such as chromium picolinate. In certain embodiments, the compositions described herein can be used in combination with other therapeutics, such as hypocholesterolemic and hypoglycemic therapeutic agents.

Compositions including chromium and histidine, chromium histidinate, chromium histidinate complexes, and combinations thereof in combination with lipophilic or slow-acting chromium complexes disclosed herein provide unexpected benefits over different sources of chromium, including various known chromium complexes, in the treatment and prevention a variety of diseases and conditions such as, but not limited to, aging, Alzheimer's Disease, cancer, cardiovascular disease, diabetic nephropathy, diabetic retinopathy, a disorder of glucose metabolism, disorders of lipid metabolism, dyslipidemia, dyslipoproteinemia, hypertension, impotence, inflammation, insulin resistance, lipid elimination in bile, obesity, oxysterol elimination in bile, pancreatitis, Parkinson's disease, a peroxisome proliferator activated receptor-associated disorder, renal disease, septicemia, Syndrome X, thrombotic disorder, and the like. Compositions and methods described herein can also be used to modulate C-reactive protein or enhance bile production in a mammal, and eliminate or reduce phospholipid in bile.

Accordingly, provided herein are methods of treating or preventing cardiometabolic syndrome or a condition associated therewith in a subject that has or is at risk of developing CMS or a condition associated therewith, by providing the subject a composition that contains a fast-acting or hydrophilic chromium complex in combination with at least one slow-acting or lipophilic chromium complex. For example, in some embodiments, an individual that has or is at risk of developing CMS or a condition associated therewith is identified, and provided a composition containing an effective dose of chromium histidinate and/or at least one other chromium complex, e.g. chromium picolinate.

Also provided herein are methods for inhibiting hepatic fatty acid and sterol synthesis in subjects in need thereof, by identifying subjects in need of inhibition of hepatic fatty acids or inhibition of sterol, and providing a therapeutically effective amount of the compositions disclosed herein to the subject. The administration or provision of a fast-acting or hydrophilic chromium complex, e.g. chromium histidinate and a slow-acting or lipophilic chromium complex, e.g. chromium picolinate, for the prevention or inhibition of fatty acid and sterol synthesis is also provided.

Also provided are methods for increasing HDL levels in a subject in need of increased HDL levels, by identifying a subject in need thereof, and providing a therapeutically effective amount of a composition disclosed herein. Accordingly, embodiments disclosed herein also relate to the treatment or prevention of diseases or disorders capable of being treated or prevented by increasing HDL levels in subjects in need thereof. For example a subject in need of increased HDL levels, e.g. a subject may believe it is in need or may self-identify or be identified using routine methods, can be provided a composition comprising, consisting essentially of, or consisting of a fast-acting or hydrophilic chromium complex, e.g. chromium histidinate and a slow-acting or lipophilic chromium complex, e.g. chromium picolinate, for increasing HDL levels.

Provided herein are methods for lowering LDL levels in subjects in need of a reduction in LDL levels by identifying a subject in need of a reduction in LDL levels, and providing a therapeutically effective amount of a composition disclosed herein to said subject. For example, a subject in need of decreased LDL levels can be provided a fast-acting or hydrophilic chromium complex, e.g. chromium histidinate, and a slow-acting or lipophilic chromium complex, e.g. chromium picolinate, for decreasing LDL levels.

Further provided herein are methods of improving endothelial function in a subject in need of improved endothelial function by identifying a subject in need of improved endothelial function, e.g. by self-identification or by routine clinical methods, and providing a therapeutically effective amount of a composition disclosed herein to said subject. For example, a subject in need of improved endothelial function can be provided a fast-acting or hydrophilic chromium complex, e.g. chromium histidinate, and a slow-acting or lipophilic chromium complex, e.g. chromium picolinate, for improving endothelial function.

Disclosed herein are methods for improving at least one of the following: blood pressure, vascular tone, vascular relaxation, and coronary blood flow in a subject in need thereof by identifying a subject in need of improved blood pressure, vascular tone, vascular relaxation, and coronary blood flow using routine clinical methods. The subject can be provided a therapeutically effective amount of a composition disclosed herein. For example a subject in need of improved blood pressure, vascular tone, vascular relaxation, and coronary blood flow can be provided a fast-acting or hydrophilic chromium complex, e.g. chromium histidinate and a slow-acting or lipophilic chromium complex, e.g. chromium picolinate, for improving blood pressure, vascular tone, vascular relaxation, and coronary blood flow.

Also provided are methods for lowering fasting and post prandial blood sugar levels, lowering serum triglyceride levels and improving insulin sensitivity in a subject in need thereof by identifying a subject in need of lower fasting and post-prandial blood sugar levels and providing a therapeutically effective amount of a composition disclosed herein to said subject. For example a subject in need of lower fasting and post-prandial blood sugar levels can be provided a composition that comprises chromium and histidine, chromium histidinate complexes, or combinations thereof in combination with at least one other slow-acting chromium complex. The administration or provision of a fast-acting or hydrophilic chromium complex, e.g. chromium histidinate and a slow-acting or lipophilic chromium complex, e.g. chromium picolinate, for lowering fasting and post-prandial blood sugar levels is also provided.

The compositions disclosed herein can improve fasting and post prandial blood insulin levels, decrease hyperinsulinemia, and decrease insulin resistance in mammals. Accordingly, some embodiments provide methods for treatment or prevention of cardiometabolic syndrome-associated disorders, such as hyperglycemia, hyperinsulinemia, or insulin resistance. A subject in need of improved fasting and post-prandial blood insulin levels, a decrease in hyperinsulinemia, or a decrease in insulin resistance may believe it is in need or may self-identify or be identified using routine methods, and is provided a therapeutically effective amount of a fast-acting and slow-acting chromium complex as disclosed herein. For example, a subject in need of improved fasting and post-prandial blood insulin levels, a decrease in hyperinsulinemia, or a decrease in insulin resistance can be provided a composition that contains chromium and histidine, chromium histidinate complexes, or combinations thereof in combination with at least one slow-acting or lipophilic chromium complex. The administration or provision of a fast-acting or hydrophilic chromium complex, e.g. chromium histidinate and a slow-acting or lipophilic chromium complex, e.g. chromium picolinate, for improving fasting and post-prandial blood insulin levels, decreasing hyperinsulinemia, and decreasing insulin resistance is also provided.

The compositions disclosed herein can decrease body fat and increase lean body mass, thereby effectuating improvements in body composition in mammals. Accordingly, some embodiments provide methods for decreasing body fat or increasing lean body mass in a subject by identifying a subject in need of a decrease in body fat or increase in lean body mass, and providing to said subject a therapeutically amount of a fast-acting chromium complex in combination with a slow-acting chromium complex. For example a subject in need of a decrease in body fat or an increase in lean muscle mass can be provided a composition that comprises chromium and histidine, chromium histidinate complexes, or combinations thereof in combination with at least one slow-acting or lipophilic chromium complex. The administration or provision of a fast-acting or hydrophilic chromium complex, e.g. chromium histidinate and a slow-acting or lipophilic chromium complex, e.g. chromium picolinate, for decreasing body fat or increasing lean muscle mass is also provided.

The compositions disclosed herein can decrease inflammatory markers, the risk of CVD and diabetes, and reduce obesity in mammals. Accordingly, some embodiments provide methods of decreasing inflammatory markers, decreasing the risk of CVD and diabetes, or reducing obesity in mammals by identifying a subject in need of a decrease in inflammatory markers, a subject at risk of CVD and diabetes, or a subject that is obese, using routine clinical methods, and providing the subject a therapeutically effective amount of a fast-acting chromium complex in combination with a slow-acting chromium complex. The administration or provision of a fast-acting or hydrophilic chromium complex, e.g. chromium histidinate and a slow-acting or lipophilic chromium complex, e.g. chromium picolinate, for decreasing inflammatory markers is also provided.

The compositions disclosed herein decrease markers associated with renal function and help in improving renal function in mammals. Accordingly, provided herein are methods for the treatment or prevention of renal disorders, by identifying a subject with or at risk of developing a renal disorder, e.g. a subject with cardiometabolic syndrome and a renal disorder, and providing a therapeutically effective amount of a composition that contains chromium and histidine, chromium histidinate complexes, or combinations thereof in combination with at least one slow-acting or lipophilic chromium complex. The administration or provision of a fast-acting or hydrophilic chromium complex, e.g. chromium histidinate and a slow-acting or lipophilic chromium complex, e.g. chromium picolinate, for improving renal function is also provided.

The compositions disclosed herein can decrease inflammatory markers associated with bone health and help in improving bone health and disorders, for example in mammals. Accordingly, some embodiments provide methods of treatment or prevention of cardiometabolic syndrome disorders with arthritis and rheumatic heart disease by identifying a subject with CMS that has or is at risk of developing arthritis or rheumatic heart using routine clinical methods, and providing the subject a therapeutically effective amount of a fast-acting or hydrophilic chromium complex, e.g. chromium histidinate and a slow-acting or lipophilic chromium complex, e.g. chromium picolinate.

The compositions disclosed herein can improve immune function associated with cardiometabolic syndrome, for example in mammals. Accordingly, provided herein are methods for treating or preventing immune function disorders, by identifying a subject with CMS that is in need of improved immune function and providing the subject a therapeutically effective amount of a fast-acting or hydrophilic chromium complex, e.g. chromium histidinate and a slow-acting or lipophilic chromium complex, e.g. chromium picolinate.

The compositions disclosed herein can improve metabolic function associated with cardiometabolic syndrome, diabetes, obesity and cardiovascular disease, for example in mammals. Accordingly, some embodiments provide methods of treatment or prevention of cardiometabolic syndrome disorders with metabolic disorders. An individual with CMS, diabetes, obesity or cardiovascular disease and poor metabolic function may believe it is in need or may self-identify or be identified using routine methods, and provided a therapeutically effective amount of a fast-acting or hydrophilic chromium complex, e.g. chromium histidinate and a slow-acting or lipophilic chromium complex, e.g. chromium picolinate.

The compositions disclosed herein can improve chromium status associated with cardiometabolic syndrome, diabetes, obesity and cardiovascular disease but not limited to other chronic conditions alone or in combination with other disorders, for example in mammals. Accordingly, some embodiments provide methods of treatment or prevention of cardiometabolic syndrome disorders with low chromium status or deficiency of chromium and methods of improving chromium depletion in tissues due to chronic conditions, by identifying subject with CMS with low chromium status, and providing the subject a therapeutically effective amount of a fast-acting or hydrophilic chromium complex, e.g. chromium histidinate and a slow-acting or lipophilic chromium complex, e.g. chromium picolinate.

The compositions disclosed herein can improve amino acid profile status and chromium absorption associated with cardiometabolic syndrome, diabetes, obesity and cardiovascular disease, for example in mammals. Accordingly, provided herein are methods of treatment or prevention of cardiometabolic syndrome disorders in subjects with low amino acid profile, deficiency of protein, or deficiency of all amino acids and to improve amino acid profile depletion by identifying a subject with CMS and low amino acid profile, protein deficiency, and/or low chromium status or levels, and providing the subject a therapeutically effective amount of a fast-acting or hydrophilic chromium complex, e.g., chromium histidinate and a slow-acting or lipophilic chromium complex, e.g., chromium picolinate.

The compositions disclosed herein can improve exchange and transport of chromium levels in the tissues associated with conditions such as cardiometabolic syndrome, diabetes, obesity and cardiovascular disease in mammals and therefore the invention also encompasses methods of improving amino acid exchange and transport of amino acids for normal functions of the organs in the body by administering to the subject a therapeutically effective dose of a fast-acting or hydrophilic chromium complex, e.g., chromium histidinate and a slow-acting or lipophilic chromium complex, e.g., chromium picolinate. Further provided are methods for improving amino acid profile or deficiency of protein or all amino acids, methods for improving amino acid profile depletion, and methods for improving amino acid absorption due to chronic conditions and to replete the amino acids levels in tissues by administering to the subject a therapeutically effective dose of a fast-acting or hydrophilic chromium complex, e.g., chromium histidinate and a slow-acting or lipophilic chromium complex, e.g., chromium picolinate.

The compositions disclosed herein improve exchange and transport of chromium levels in the tissues associated with conditions such as aging, and chronic diseases such as cardiometabolic syndrome, diabetes, obesity and cardiovascular disease in mammals. Accordingly, some embodiments relate to methods improving chromium exchange along with other nutrients and transport of chromium for normal functions of the organs in the body to the tissues and to improve chromium status or deficiency of chromium or to improve chromium levels in tissues such as hair, skin, toenails, serum, blood, plasma and enhancing tissue concentrations in the organs including brain, heart, lung, liver, kidneys, spleen, and aorta. Preferably, the methods for improving chromium status and repleting chromium in the tissues and improving chromium levels or status in physiology and biochemistry due to chronic conditions by administering a therapeutically effective dose of a fast-acting or hydrophilic chromium complex, e.g., chromium histidinate and a slow-acting or lipophilic chromium complex, e.g., chromium picolinate.

The compositions disclosed herein favorably alter lipid metabolism in mammals with dyslipidemia at least in part by enhancing oxidation of fatty acids through the ACC/malonyl-CoA/CPT-I regulatory axis. Accordingly, provided herein are methods of treating dyslipidemia by identifying a subject with a poor lipid profile, and providing a therapeutically effective amount of a composition described herein to the subject. For example, an individual with dyslipidemia can be provided a a fast-acting or hydrophilic chromium complex, e.g., chromium histidinate and a slow-acting or lipophilic chromium complex, e.g., chromium picolinate. The fast-acting or hydrophilic chromium complex can be formulated with the slow-acting or lipophilic chromium complex. Alternatively, the fast-acting and slow-acting chromium complexes can be administered separately.

Further embodiments provide methods for reducing the abdominal fat in subjects in need thereof by identifying subject in need of abdominal fat-content reduction and providing the subject a therapeutically effective amount of a fast-acting or hydrophilic chromium complex, e.g., chromium histidinate and a slow-acting or lipophilic chromium complex, e.g., chromium picolinate.

Provided herein are methods for reducing the total serum cholesterol of a subject. A subject in need of a reduction in serum cholesterol levels may believe it is in need or may self-identify or be identified, and provided a therapeutically effective amount of a a fast-acting or hydrophilic chromium complex, e.g., chromium histidinate and a slow-acting or lipophilic chromium complex, e.g., chromium picolinate, for lowering cholesterol levels is provided.

DETAILED DESCRIPTION OF THE PREFERRED EMBODIMENT

Figure 1:
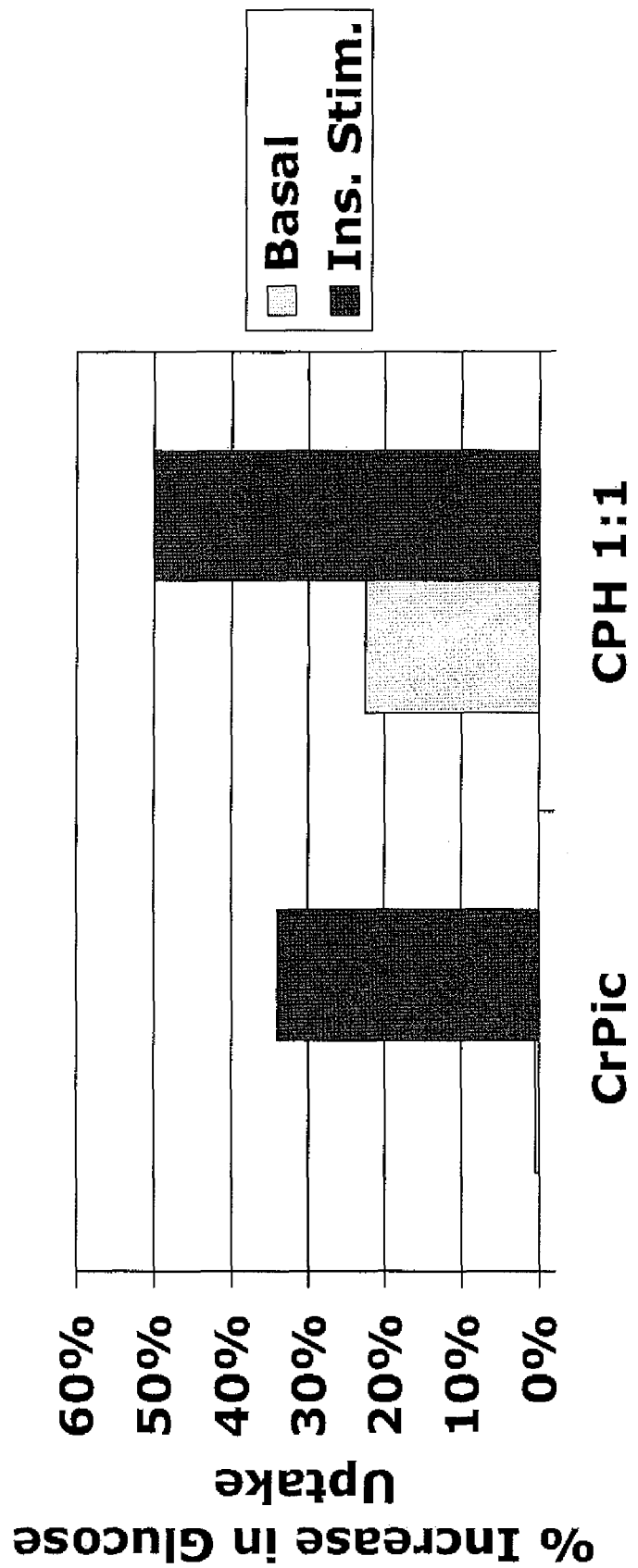
FIG. 1 is a bar graph showing the difference in glucose uptake by unstimulated and insulin-stimulated skeletal muscle cells cultured in the presence of chromium picolinate or the combination of chromium picolinate/chromium histidinate (1:1) compared to untreated cultures.

The present invention is based, in part, on the novel and unexpected discovery that the combination of a slow-acting, lipophilic chromium complex with a fast-acting, hydrophilic chromium complex provides unexpected and improved properties when compared to either a fast-acting or a slow-acting chromium complex alone. Accordingly, described herein are compositions that provide for improved administration of chromium to an individual, and methods of uses thereof, that include at least one slow-acting, lipophilic chromium complex and at least one fast-acting, hydrophilic chromium complex.

In some embodiments, the compositions can comprise, consist essentially of, or consist of at least two components: a hydrophilic chromium complex and a lipophilic chromium complex. In other embodiments, the compositions can include a first chromium complex and a second chromium complex, wherein the first chromium complex is absorbed more quickly ("fast-acting") than the second chromium complex ("slow-acting").

As used herein, the phrase "over a period of time," can refer to a period of minutes, hours or days. For example, over a period of time can refer to at least 10 minutes, at least 15 minutes, at least 30 minutes, at least 60 minutes, at least 75 minutes, at least 90 minutes, at least 105 minutes, at least 120 minutes, at least 3 hours, at least 4 hours, at least 5 hours, at least 6 hours, at least 7 hours, at least 8 hours, at least 9 hours, at least 10 hours, at least 12 hours, at least 14 hours, at lest 16, hours, at least 18 hours, at least 20 hours, at least 22 hours, at least one day, at least two days, at least three days, at least 4 days, at least 5 days, at least 6 days, at least a week, or any interval of time in between. In other words, the chromium from the composition can be absorbed by the individual to whom it is administered over a period of at least 10 minutes, at least 15 minutes, at least 30 minutes, at least 60 minutes, at least 75 minutes, at least 90 minutes, at least 105 minutes, at least 120 minutes, at least 3 hours, at least 4 hours, at least 5 hours, at least 6 hours, at least 7 hours, at least 8 hours, at least 9 hours, at least 10 hours, at least 12 hours, at least 14 hours, at lest 16, hours, at least 18 hours, at least 20 hours, at least 22 hours, at least one day, at least two days, at least three days, at least 4 days, at least 5 days, at least 6 days, at least a week, or any interval of time in between.

In some embodiments, the compositions provide bioavailable chromium for a period of time that is about the same as the period of time that a "slow-acting" chromium complex alone provides bioavailable chromium. The term "bioavailable," in reference to chromium as used herein is meant to refer to the amount of chromium that is absorbed by an individual. In preferred embodiments, the compositions provide bioavailable chromium over a total period of time that is greater than the period of time as that of the "slow-acting" chromium complex alone provides bioavailable chromium. For example, the compositions described herein can provide bioavailable chromium for a period of time that is at least 10 minutes, at least 15 minutes, at least 30 minutes, at least 60 minutes, at least 75 minutes, at least 90 minutes, at least 105 minutes, at least 120 minutes, at least 3 hours, at least 4 hours, at least 5 hours, at least 6 hours, at least 7 hours, at least 8 hours, at least 9 hours, at least 10 hours, at least 12 hours, at least 14 hours, at lest 16, hours, at least 18 hours, at least 20 hours, at least 22 hours, at least one day, at least two days, at least three days, at least 4 days, at least 5 days, at least 6 days, at least a week, or any interval of time in between, greater than the "slow-acting" chromium complex alone. By administrating a slow-acting chromium complex together with a fast-acting chromium complex, we have been able to achieve a sustained release and absorption of chromium over a period of time.

As used herein, the term "hydrophilic chromium complex" or "fast acting chromium complex" refers to a chromium complex that is charged at physiological pH, or has polar properties. Non-limiting examples of hydrophilic, fast-acting chromium complexes include chromium acetate, chromium chloride, chromium histidinate and chromium nicotinate, and the like, or any pharmaceutically acceptable salts, hydrates, solvates, or mixtures thereof.

The term "lipophilic chromium complex" or "slow-acting chromium complex" refers to a chromium complex that is not charged at physiological pH, and that does not have polar properties. Chromium picolinate, and any pharmaceutically acceptable salts, hydrates, or solvates thereof, is a non limiting example of a lipophilic, slow-acting chromium complex.

In preferred embodiments, the hydrophilic chromium complex or the "fast-acting" chromium complex is chromium histidinate, chromium trihistidinate, or chromium polyhistidinate, or any combination thereof. Preferably, the lipophilic chromium complex or the "slow-acting" chromium complex is chromium picolinate.

The terminology used in the description presented herein is not intended to be interpreted in any limited or restrictive manner, simply because it is being utilized in conjunction with a detailed description of certain specific embodiments described herein. Furthermore, embodiments described herein can include several novel features, no single one of which is solely responsible for its desirable attributes or which is essential to practicing the invention herein described. As used herein, the term "slow-acting chromium complexes" or "slow-acting chromium complex" includes trivalent chromium complexes, such as chromium picolinate, chromic tripicolinate, and other lipophilic chromium complexes, whether now known or developed in the future.

The present invention is based, in part, on the novel and unexpected discovery that when a subject is administered a fast-acting chromium complex and a slow-acting chromium complex, the symptoms and incidence of insulin resistance are lowered. Accordingly, some embodiments provide a method for the inhibition or reduction of insulin resistance, or lowering the risk of developing insulin resistance or related symptoms by lowering glucose and lipids and improving insulin sensitivity by administering a fast-acting and a slow-acting chromium complex, e.g. chromium histidinate and chromium picolinate.

As used herein, the term "altering lipid metabolism" indicates an observable (measurable) change in at least one aspect of lipid metabolism, including but not limited to total blood lipid content, blood HDL cholesterol, blood LDL cholesterol, blood VLDL cholesterol, blood triglyceride, blood Lp(a), blood apo A-I, blood apo E and blood non-esterified fatty acids, esters of fatty acids, isomers, isoforms and ratios and improving ratios for reducing chronic disease risk but not limited to diabetes, obesity, hypertension, coronary heart disease and cardiovascular disease.

As used herein, the term "altering glucose metabolism" indicates an observable (measurable) change in at least one aspect of glucose metabolism, including but not limited to total blood glucose content, blood insulin, the blood insulin to blood glucose ratio, glycosylated hemoglobin, HOMAIR, beta cell function, composite of insulin sensitivity index, hyperglycemia, hyperglycemia, hypoglycemia, hormones, enhancing enzyme activities, improving hormonal balance caused due to insulin resistance, abnormal glucose metabolism, lipodystrophy, reducing brain insulin resistance, insulin sensitivity, and oxygen consumption. Abnormal glucose metabolism in conditions like polycystic ovary syndrome, HIV, HIV lipodystrophy, Alzheimer's disease, mental health disorders, lipodystrophy, hormonal imbalance conditions, hypertension, obesity and cardiovascular disease and cardiometabolic syndrome.

"Insulin resistance" refers to a condition characterized by decreased insulin function and hyperinsulinemia, caused or exacerbated by drugs and disease conditions such to obesity, diabetes, CVD in a human or other animal. Examples of drugs which induce insulin resistance include, without limitation, statin drugs such as simvastatin, cerivastatin, pravastatin, atorvastatin, fluvastatin, and lovastatin; non-steroidal anti-inflammatory drugs such as cimicifuga, choline salicylate-magnesium salicylate, diclofenac sodium, diclofenac potassium, diflunisal, etodolac, fenoprofen calcium, floctafenine, flurbiprofen, ibuprofen, indomethacin, ketoprofen, ketorolac tromethamine, magnesium salicylate, mefenamic acid, nabumetone, naproxen, naproxen sodium, oxyphenbutazone, phenylbutazone, piroxicam, salsalate, sodium salicylate, sulindac, tenoxicam, taiprofenic acid, and tolmetin sodium; steroids such as hydrocortisone, dexamethasone, and methylprednisolone; contraceptives including oral contraceptives such as estrogen, progesterone and progestin as well as implantable contraceptives such as levonorgestrel, etonogestrel, nomegestrol acetate, and nestorone; hormone replacement therapy (HRT) drugs including conjugated equine estrogens, esterified estrogens, estradiol, estrone, synthetic conjugated estrogens, estropipate, estropipate, ethinyl estradiol, norethindrone, medroxyprogesterone acetate, progestin, natural progesterone, tamoxifen, testosterone, and raloxifene; beta blocker drugs including acebutolol, atenolol, betaxolol, bucinodol, carteolol, labetalol, metoprolol, nadolol, penbutolol, pindolol, propanolol, and timolol; and diuretics. Three primary types of diuretics exist which include thiazides, loop diuretics, and potassium sparing agents. As used herein, the term "diuretic" or "diuretics" includes, without limitation, hydrochlorothiazide, chlorthalidone, chlorothiazide, indapamide, metolazone, amiloride, spironolactone, triamterene, furosemide, bumetanide, ethacrynic acid, and torsemide. Certain immunosuppressive drugs such as prednisolone, cyclosporin A, and tacromlimus and potassium channel modulators such as nicorandil are also included in the definition of drugs which induce insulin resistance, such as, for example, antidepressants. The above list is provided for example purposes only and it is understood that the definition of "drug which induces insulin resistance" includes those drugs which induce insulin resistance that are not specifically listed above, as well as those drugs which are found to induce insulin resistance, whether in existence today or developed in the future. Examples of diet which induce insulin resistance include diets high in fats, carbohydrates, low dietary fiber, high glycemic index foods, high fructose in the functional foods, beverages, and bars.

Other embodiments relate to the use of compositions comprising, consisting essentially of, or consisting of chromium and histidine, chromium histidinate complex, chromium trihistidinate, or chromium poly histidinate complex, or combinations thereof, including pharmaceutically acceptable salts, hydrates, solvates, or mixtures thereof in combination with a second slow-acting chromium complex for the treatment or prevention of cardiometabolic syndrome and related conditions, diseases, and disorders.

The term "treating" or "treatment" does not necessarily mean total cure. Any alleviation of any undesired signs or symptoms of the disease to any extent or the slowing down of the progress, or even prevention of the disease or condition can be considered treatment.

Other embodiments relate to the use of compositions comprising, consisting essentially of, or consisting of chromium and histidine, chromium histidinate complex, chromium trihistidinate, or chromium poly histidinate complex, or combinations thereof, including pharmaceutically acceptable salts, hydrates, solvates, or mixtures thereof in combination with a second slow-acting chromium complex for the maintenance of healthy or normal serum glucose levels, serum cholesterol levels, serum triglyceride levels, or free fatty acid levels and/or the prevention of the development of hyperglycemia, dyslipidemia, high cholesterol, high triglycerides, or high free fatty acid levels. In some embodiments, the subject may have normal blood glucose, cholesterol, triglyceride, or free fatty acid levels. Accordingly, some embodiments relate to maintenance of fasting plasma glucose levels at less than about 100 mg/dL (5.55 mmol per liter) in a subject, for example, in a healthy subject. Some embodiments relate to maintenance of total serum cholesterol levels below about 200 mg/dL, maintenance of serum HDL levels above about 40-50 mg/dL; maintenance of serum LDL levels below about 100 mg/dL, maintenance of serum triglycerides at below about 150 mg/dL, or the like.

The Role of Histidine/Histidinate

Histidine is one of the 20 most common natural amino acids present in proteins. In the nutritional sense, in humans, histidine is considered an essential amino acid for normal healthy function. The imidazole side chains and the relatively neutral pKa of histidine (ca 6.0) mean that relatively small shifts in cellular pH will change its charge. For this reason, this amino acid side chain finds its way into considerable use as a coordinating ligand in metalloproteins, and also as a catalytic site in certain enzymes. The imidazole side chain has two nitrogens with different properties: one is bound to hydrogen and donates its lone pair to the aromatic ring and as such is slightly acidic; the other one donates only one electron to the ring so it has a free lone pair and is basic. These properties are exploited in different ways in proteins. In catalytic triads, the basic nitrogen of histidine is used to abstract a proton from serine, threonine or cysteine to activate it as a nucleophile. In a histidine proton shuttle, histidine is used to quickly shuttle protons, it can do this by abstracting a proton with its basic nitrogen to make a positively-charged intermediate and then use another molecule, a buffer, to extract the proton from its acidic nitrogen. In carbonic anhydrases, a histidine proton shuttle is utilized to rapidly shuttle protons away from a zinc-bound water molecule to quickly regenerate the active form of the enzyme. The amino acid is a precursor for histamine and carnosine biosynthesis.

Histidine has two enantiomeric forms: D-histidine and L-histidine. The structure of histidine is shown below. Histidine is a basic, essential amino acid that is also a precursor of histamine, a compound released by immune system cells during an allergic reaction. Histamine is needed for growth and for the repair of tissue, as well as the maintenance of the myelin sheaths that act as protector for nerve cells. It is further required for the manufacture of both red and white blood cells, and helps to protect the body from damage caused by radiation and in removing heavy metals from the body. In the stomach, histidine is also helpful in producing gastric juices, and people with a shortage of gastric juices or suffering from indigestion, may also benefit from this nutrient. Histidine is also used for sexual arousal, functioning and enjoyment. Histidinemia is an inborn error of the metabolism of histidine due to a deficiency of the enzyme histidase, where high levels of histidine are found in the blood and urine, and may manifest in speech disorders and mental retardation.

The compositions described herein that comprise chromium and histidine, or chromium histidinate complexes, such as chromium histidinate chromium trihistidinate, and chromium polyhistidinate, or combinations thereof, e.g. including components of some of the compositions disclosed herein for the administration of chromium over a period of time, exhibit improved absorption in mammals over other known chromium complexes. In particular, the compositions described herein show superior absorption and intracellular release of chromium from the histidinate complex.

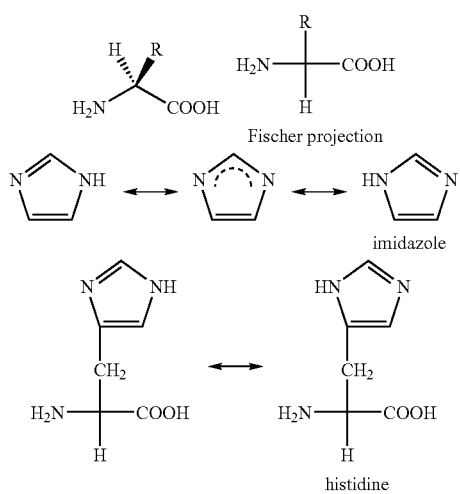

histidine

Several of the compositions disclosed herein can include chromium and histidine, or chromium histidinate complexes in combination with other chromium complexes including chromium picolinate, chromium nicotinate, chromium chloride, tri-chromium(III) oxo acetate cluster ([Cr(3)O(OAc)(6)](+)), biomimetic cation [Cr(3)O(O(2)CCH(2)CH(3))(6)(H(2)O)(3)](+) and chromium triphenylanine, and any other chromium complex now known or discovered in the future.

The compositions described herein can contain one or more chiral centers and/or double bonds and, therefore, exist as stereoisomers, such as double-bond isomers (i.e., geometric isomers), enantiomers, or diastereomers. The chemical structures depicted herein, and therefore the compositions disclosed herein, encompass all of the corresponding compounds' or compositions' enantiomers and stereoisomers, that is, both the stereomerically pure form (e.g., geometrically pure, enantiomerically pure, or diastereomerically pure) and enantiomeric and stereoisomeric mixtures.

As used herein, a composition that "substantially" comprises a compound means that the composition contains more than about 80% by weight, more preferably more than about 90% by weight, even more preferably more than about 95% by weight, and most preferably more than about 97% by weight of the compound. As used herein, a composition that "substantially" comprises a chromium complex refers to a composition that contains more than or equal to 7.0% of trivalent or dietary chromium. Preferably, a certificate of analysis for the compositions disclosed herein indicate that the compositions are negative for microbial growth, yeast and mold should be present in less than 300 cells/g and the toxic metals should be less than 1 ppm.

In some embodiments, the compositions disclosed herein are in the form of pharmaceutically effective salts. The phrase "pharmaceutically acceptable salt(s)," as used herein includes, but is not limited to, salts of acidic or basic groups that may be present in the compositions disclosed herein. Compounds that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds present in the compositions disclosed herein that include an amino moiety also can form pharmaceutically acceptable salts with various amino acids, in addition to the acids mentioned above. Compounds present in the compositions disclosed herein that are acidic in nature are capable of forming base salts with various pharmacologically acceptable cations. Non limiting examples of such salts include alkali metal or alkaline earth metal salts and, particularly, calcium, magnesium, sodium lithium, zinc, potassium, silicon, phosphorus and iron salts.

As used herein, the term "hydrate" means a compound or a salt thereof, that further includes a stoichiometric or non-stoichiometric amount of water bound by non-covalent intermolecular forces. The term hydrate includes solvates, which are stoichiometric or non-stoichiometric amounts of a solvent bound by non-covalent intermolecular forces. Preferred solvents are volatile, non-toxic, and/or acceptable for administration to humans in trace amounts.

The amount of a compound of the invention that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each circumstances. However, suitable dosage ranges for oral administration are generally about 0.001 milligram to 5000 milligrams of a total chromium complex (e.g. fast-acting and slow-acting combined) per kilogram body weight. In preferred embodiments, the oral dose is 0.01 milligram total chromium complex to 1000 milligrams per kilogram body weight, more preferably 0.1 milligram to 100 milligrams per kilogram body weight, more preferably 0.5 milligram to 25 milligrams per kilogram body weight, and yet more preferably 1 milligram to 10 milligrams per kilogram body weight. The dosage amounts described herein refer to total amounts administered; that is, if more than one chromium complex or more than one composition disclosed herein is administered, the preferred dosages correspond to the total amount of the compositions disclosed herein administered. Oral compositions preferably contain 10% to 95% active ingredient.

The compositions disclosed herein can preferably be formulated with other active ingredients as a slow-acting agent or long acting agent in addition to drugs or alone before meals and/or after meals. Effective doses may be extrapolated from dose-response curves derived from in vitro or animal model test systems. Such animal models and systems are well known in the art.

In accordance with the methods disclosed herein, the amount of chromium provided by the compositions that comprise fast-acting and slow-acting complexes disclosed herein can be at least 50 µg per day, for example at least 60 µg, at least 70 µg, at least 80 µg, at least 90 µg, at least 100 µg, at least 125 µg, at least 150 µg, at least 200 µg, at least 250 µg, at least 300 µg, at least 350 µg, at least 400 µg, at least 450 µg, at least 500 µg, at least 550 µg, at least 600 µg, at least 650 µg, at least 700 µg, at least 750 µg, at least 800 µg, at least 850 µg, at least 900 µg, at least 950 µg, at least 1,000 µg, at least 1500 µg, at least 2,000 µg, at least 2500 µg, at least 3000 µg, at least 3500 µg, at least 4000 µg, at least 4500 µg or at least 5000 µg chromium complex/day.

The fast-acting and the slow-acting chromium complexes can be provided to a subject such that the ratio of chromium in the form of a "fast-acting" chromium complex to the chromium in the form of a "slow-acting" chromium complex is anywhere from 10:1 to 1:10, e.g., 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, or any fraction in between. In some embodiments, the ratio of chromium provided in the form of a fast-acting chromium complex to the slow-acting chromium complex is 1:1.

By way of example, the level of chromium used for supplementation in order to inhibit the onset of insulin resistance is at least about 50 µg/day. Chromium picolinate and chromium chloride have been administered to rats at levels several thousand times the upper limit of the estimated safe and adequate daily dietary intake (ESADDI) for chromium for humans (based on body weight) without toxic effects. R. Anderson et al., Lack of Toxicity of Chromium Chloride and Picolinate, 16 J. Am. Coll. Nutr. 273-279 (1997). While the level of chromium, in the form of fast-acting and slow-acting chromium complexes, used for supplementation may be within several thousand times the upper limit of the ESADDI, preferably, the total amount of chromium provided by the fast-acting and slow-acting complexes is between about 50 and 2,000 µg/day. More preferably, the amount of total chromium provided by the fast-acting and slow-acting complexes is between about 300 and 1,000 µg/day. Most preferably, the amount of total chromium is between about 400 and 1,000 µg/day. In a particularly preferred embodiment, the amount of total chromium is between about 600 and 1,000 µg/day. These doses are based on a 70 kg adult human, and that the dose can be applied on a per-kilogram basis to humans or animals of different weights.

In some embodiments, the amount of fast-acting chromium complex and the amount of slow-acting chromium complex in a composition provide a greater than additive effect in lowering serum glucose levels than either complex alone. In some embodiments, the amount of fast-acting chromium complex and the amount of slow-acting chromium complex in a composition provide a synergistic or greater than additive effect in improving insulin sensitivity. In some embodiments, the amount of fast-acting chromium complex and the amount of slow-acting chromium complex in a composition provide a greater than additive effect in treating dyslipidemia. In some embodiments, the amount of fast-acting chromium complex and the amount of slow-acting chromium complex in a composition provide a greater than additive effect in lowering serum cholesterol, lowering serum triglycerides, lowering free fatty acid levels, or increasing HDL levels. In some embodiments, the amount of fast-acting chromium complex and the amount of slow-acting chromium complex in a composition provide a greater than additive effect in increasing lean muscle mass.

In some embodiments, the compositions disclosed herein are provided in an amount effective for the prevention of insulin resistance. As used herein, the term "insulin resistance (IR)" refers to a physiologically abnormal state in which cells do not respond appropriately to insulin, such that glucose in the blood cannot efficiently enter cells and, therefore, leads to hyperglycemia. Insulin resistance is believed to affect one in three adult Americans which amounts to approximately 99.3 million Americans with some degree of insulin resistance. The cardiovascular and metabolic disturbances associated with IR can individually and interdependently lead to a substantial increase in cardiovascular disease (CVD) morbidity and mortality, making the cardiometabolic syndrome an established and strong risk factor for premature and severe CVD and stroke. For example, in some embodiments, a subject is provided a composition comprising a fast-acting chromium complex chromium such as histidinate in combination with a sufficient amount of a slow-acting chromium complex to inhibit or reduce the risk of the onset of insulin resistance are provided. The fast-acting chromium complex can be formulated together with the slow-acting chromium complex or the fast-acting chromium complex can be administered separately before, substantially contemporaneously with or after the slow-acting chromium complex. The assessment of the affects of the compositions on insulin resistance can readily be determined using routine techniques known to those skilled in the art, and described, for example, in U.S. patent application Ser. No. 10/090,038, herein incorporated by reference in its entirety. Preferably, the sufficient amount of chromium provided by the fast-acting and slow-acting chromium complexes and contained in the composition is between about 50 µg and 2000 µg.

Advantageously, an individual is administered a pharmaceutically effective dose of a hydrophilic chromium complex such as chromium histidinate in combination with at least one other lipophilic chromium complex. In some embodiments, a composition the fast-acting and a slow-acting chromium complexes are administered substantially simultaneously. In an alternative embodiment, the fast-acting, hydrophilic and slow-acting, lipohilic chromium complexes are provided to the subject sequentially in either order. If administered separately, the fast-acting and slow-acting chromium complex should be given in a temporally proximate manner, e.g., within a twenty-four hour period. More particularly, the a fast-acting and a slow-acting chromium complex) can be given within one hour of each other. One of skill in the art will appreciate that other components may be added separately or incorporated into a single formulation to enhance the effects of chromium.

In some embodiments, the compositions disclosed herein can be provided prior to or concomitantly with an insulin resistance-inducing food. Insulin resistance-inducing foods generally have high glycemic indexes, e.g. over 50. In other embodiments, the compositions are provided after the insulin resistance inducing food. In embodiments wherein the compositions and the insulin resistance-inducing foods are not provided concomitantly, the composition and the food are preferably provided in a temporally proximate manner, e.g. within twenty four hours, and more preferably within one hour.

In some embodiments, uncomplexed chelating agents are advantageously included in the compositions to facilitate absorption of other ingested chromium as well as other metals including, but not limited to, copper, iron, magnesium, manganese, and zinc. Suitable chelating agents include histidine, any essential amino D or L amino acids, tri amino acid formulae including but not limited to, triphenylalanine, trihistidine, triarginine, picolinic acid, nicotinic acid, or both picolinic acid and nicotinic acid. Thus, the compositions of the disclosed invention are readily absorbable forms of chromium complex which also facilitate absorption of other essential metals in the human diet. In some embodiments, certain chelating agents may be added to facilitate absorption of the chromium complex, or combination of chromium complexes in the compositions disclosed herein. Chelating agents such as histidine, picolinic acid and nicotinic acid are available from many commercial sources, including Sigma-Aldrich (St. Louis, Mo.) (picolinic acid; catalog No. P5503; nicotinic acid; catalog No. PN4126). Preferably, the ratio of either the fast-acting, or slow-acting, or the combination of the fast-acting and slow-acting chromium complex to the chelating agent from about 10:1 to about 1:10 (w/w), more preferably from about 5:1 to about 1:5 (w/w). Alternatively, the molar ratio of chromium complex to the uncomplexed chelating agent is preferably 1:1, and may be from about 5:1 to about 1:10. The chelating agents with D or L amino acid and or with tri or mono and di forms of chromium complex with tri amino acid or one or more amino acids but not limited to chromium triphenylanine, chromium trihistidine, chromium polyphenylanine, chromium poly hisitidine, chromium polynicotinate, chromium diphenylananine, chromium dipicolinic acid, chromium dihisitidine etc. More than one chelating agent, e.g., both nicotinic and picolinic acid can be included in the compositions disclosed herein, or administered to subject in the methods described herein.

The administration of the compositions disclosed herein can be by any of the methods of administration described below or by delivery methods known by one of skill in the art. The compositions may be administered orally, through parenteral nutrition, e.g., feeding tube or intravenously, and through other known means. Chromium histidinate in combination with other chromium complexes or essential nutrients but not limited to fatty acids, carbohydrates, minerals and vitamins etc. is a particularly preferred source fast-acting chromium complex due to its high level of bioavailability, but other fast-acting, hydrophilic chromium complex can also be used.

For oral administration, the compositions disclosed herein can be provided as a tablet, aqueous or oil suspension, dispersible powder or granule, emulsion, hard or soft capsule, syrup, elixir, or beverage. Compositions intended for oral use can be prepared according to any method known in the art for the manufacture of pharmaceutically acceptable compositions and such compositions may contain one or more of the following agents: sweeteners, flavoring agents, coloring agents and preservatives. The sweetening and flavoring agents will increase the palatability of the preparation. Tablets containing chromium complexes in admixture with nontoxic pharmaceutically acceptable excipients suitable for tablet manufacture are acceptable. Pharmaceutically acceptable vehicles such as excipients are compatible with the other ingredients of the formulation (as well as non-injurious to the patient). Such excipients include inert diluents such as calcium carbonate, sodium carbonate, lactose, calcium phosphate or sodium phosphate; granulating and disintegrating agents, such as corn starch or alginic acid; binding agents such as starch, gelatin or acacia; and lubricating agents such as magnesium stearate, stearic acid or talc. Tablets can be uncoated or can be coated by known techniques to delay disintegration and absorption in the gastrointestinal tract and thereby provide a sustained action over a longer period of time. For example, a time delay material such as glyceryl monostearate or glyceryl distearate alone or with a wax can be employed.

Formulations for oral use can also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil. Aqueous suspensions can contain the chromium complex of the invention in admixture with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

Oil suspensions can be formulated by suspending the active ingredient in a vegetable oil, such as arachis oil, olive oil, sesame oil or coconut oil, or in a mineral oil such as liquid paraffin. The oil suspension can contain a thickening agent, such as beeswax, hard paraffin or cetyl alcohol. Sweetening agents, such as those set forth above, and flavoring agents can be added to provide a palatable oral preparation. These compositions can be preserved by an added antioxidant such as ascorbic acid. Dispersible powders and granules of the invention suitable for preparation of an aqueous suspension by the addition of water provide the active ingredient in admixture with a dispersing or wetting agent, a suspending agent, and one or more preservatives. Additional excipients, for example sweetening, flavoring and coloring agents, can also be present.

Syrups and elixirs can be formulated with sweetening agents, such as glycerol, sorbitol or sucrose. Such formulations can also contain a demulcent, a preservative, a flavoring or a coloring agent.

The chromium complex preparations for parenteral administration can be in the form of a sterile injectable preparation, such as a sterile injectable aqueous or oleaginous suspension. This suspension can be formulated according to methods well known in the art using suitable dispersing or wetting agents and suspending agents. The sterile injectable preparation can also be a sterile injectable solution or suspension in a non-toxic parenterally-acceptable diluent or solvent, such as a solution in 1,3-butanediol. Suitable diluents include, for example, water, Ringer's solution and isotonic sodium chloride solution. In addition, sterile fixed oils can be employed conventionally as a solvent or suspending medium. For this purpose, any bland fixed oil can be employed including synthetic mono or diglycerides. In addition, fatty acids such as oleic acid can likewise be used in the preparation of injectable preparations.

The pharmaceutical compositions can also be in the form of oil-in-water emulsions. The oily phase can be a vegetable oil, such as olive oil or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain sweetening and flavoring agents.

It will be appreciated by the skilled artisan that the amount of chromium histidine in combination with chromium complex that can be combined with the carrier material to produce a single dosage form will vary depending upon the host treated and the particular mode of administration.

When administered to a mammal, e.g., to an animal for veterinary use or for improvement of livestock, or to a human for therapeutic use, the compositions disclosed herein are administered in isolated form or as the isolated form in a therapeutic composition. As used herein, "isolated" means that the compositions disclosed herein are separated from other components of either (a) a natural source, such as a plant or cell or food, preferably bacterial culture, or (b) a synthetic organic chemical reaction mixture. Preferably, via conventional techniques, the compositions disclosed herein are purified. As used herein, "purified" means that when isolated, the isolate contains at least 95%, preferably at least 98% of the composition.

In some embodiments, the compositions disclosed herein are provided to the subject orally. In other embodiments, the compositions disclosed herein are provided by any other convenient route, for example, by intravenous infusion or bolus injection, by absorption through epithelial or mucocutaneous linings (e.g., oral mucosa, rectal and intestinal mucosa, etc.) and can be administered together with another biologically active agent. Administration can be systemic or local. Various delivery systems useful in the methods disclosed herein include for example, encapsulation in liposomes, microparticles, microcapsules, capsules, etc., and can be used to administer a compound of the invention. In certain embodiments, more than one composition disclosed herein is administered to an individual.

Other modes of administration useful in the methods include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The preferred mode of administration is left to the discretion of the professional, and will depend in-part upon the site of the condition to be treated. In most instances, administration will result in the release of the compositions disclosed herein into the bloodstream.

In specific embodiments, it can be desirable to administer one or more compositions disclosed herein locally to the area in need of treatment. This can be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of an atherosclerotic plaque tissue In certain embodiments, for example, for the treatment of Alzheimer's disease, it may be desirable to introduce one or more compositions disclosed herein into the central nervous system by any suitable route, including intraventricular, intrathecal or epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compositions disclosed herein can be formulated as a suppository, with traditional binders and vehicles such as triglycerides.

Preferably, the compositions disclosed herein are formulated with a pharmaceutically acceptable vehicle. As used herein, the term "pharmaceutically acceptable" means approved by a regulatory agency of the Federal or a state government or listed in the U.S. Pharmacopeia or other generally recognized pharmacopeia for use in animals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the compositions of the invention and pharmaceutically acceptable vehicles are preferably sterile. Water is a preferred vehicle when the compositions of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use.

In some embodiments, the compositions disclosed herein are formulated for oral delivery, for example in the form of tablets, lozenges, aqueous or oily suspensions, granules, powders, emulsions, capsules, syrups, or elixirs. Compounds and compositions described herein for oral delivery can also be formulated in foods and food mixes. Orally administered compositions can contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compounds and compositions described herein. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate can also be used. Oral compositions can include standard vehicles such as mannitol, lactose, starch, magnesium stearate, sodium saccharine, cellulose, magnesium carbonate, etc. Such vehicles are preferably of pharmaceutical grade.

In some embodiments, the compositions described herein can be in the form of nutraceutical packs not limited to functional foods, beverages, bars, dietary supplements, capsules, powder form or gelatin form, pharmaceutical packs or kits comprising one or more containers filled with one or more compositions disclosed herein. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the kit contains more than one compound described herein. In another embodiment, the kit comprises a compound described herein and another lipid-mediating compound, glycemic control and antihypertensive drugs, including but not limited to insulin, statin, a thiazolidinedione, or a fibrate or dietary modifications.

The compositions disclosed herein can be assayed in vitro and in vivo, for the desired therapeutic or prophylactic activity, prior to use in humans. For example, in vitro assays can be used to determine whether administration of a specific compound described herein or a combination of compositions disclosed herein is preferred for lowering fatty acid synthesis. The compositions disclosed herein also be demonstrated to be effective and safe using animal model systems.

Throughout the specification there are references to identifying a subject in need of administration of a chromium complex which includes a hydrophilic chromium complex and a lipophilic chromium complex. The term identification is not intended to be limiting and includes in each instance a belief by the subject that the chromium complexes will benefit the subject, self-identification, and identification by third party using various techniques. The identification may be of at least one condition selected from the group consisting of: insulin resistance, cardiovascular disease, progressive renal disease, end stage renal disease, endothelial dysfunction, left ventricular hypertrophy, cardiac hyperreactivity, dyslipidemia, hyperglycemia, enhanced rennin angiotensin activity, aldosterone syndrome, impaired pressure natriuresis, chronic low grade inflammation, diabetes mellitus, hypertension, atherosclerosis, micoralbuminuria, obesity, depression, Syndrome X, and polycystic ovary syndrome. The identification may comprise identifying an individual that is taking a composition comprising a compound selected from the group consisting of: non-steroidal anti inflammatory compounds, oral contraceptives, implantable steroid contraceptives, hormone replacement therapy, beta blockers, potassium channel openers and immunosuppressive drugs.

Therapeutic Uses of Chromium Histidine/Histidinate

In accordance with the methods disclosed herein, a composition comprising, consisting essentially of, or consisting of a chromium and histidine, chromium histidinate complex, chromium trihistidinate, or chromium polyhistidinate complex, or any combination thereof, and a second chromium complex comprising, consisting essentially of or consisting of a slow-acting chromium complex such as chromium picolinate is provided to a subject, such as a mammal, with or at risk of aging, Alzheimer's Disease, cancer, cardiovascular disease, diabetic nephropathy, diabetic retinopathy, a disorder of glucose metabolism, dyslipidemia, dyslipoproteinemia, enhancing bile production, enhancing reverse lipid transport, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), a thrombotic disorder, gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis and/or other soft tissue rheumatism.

As used herein, the term "treatment" or "treating" refers to an amelioration of a disease or disorder, or at least one discernible symptom thereof. The term "treatment" or "treating" refers to inhibiting the progression of a disease or disorder, either physically, e.g. stabilization of a discernible symptom, or physiologically, e.g. stabilization of a physical parameter, or both.

In certain embodiments, the compositions disclosed herein are provided to a subject, such as a mammal, as a preventative measure against such diseases. As used herein, "prevention" or "preventing" refers to a reduction of the risk of acquiring a given disease or disorder alone or in combination with other clinical condition.

In some embodiments, the compositions disclosed herein are provided as a preventative measure to a patient, preferably a human having a genetic predisposition to a aging, Alzheimer's Disease, cancer, cardiovascular disease, diabetic nephropathy, diabetic retinopathy, a disorder of glucose metabolism, dyslipidemia, dyslipoproteinemia, enhancing bile production, enhancing reverse lipid transport, hypertension, impotence, inflammation, insulin resistance, lipid elimination in bile, modulating C-reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), a thrombotic disorder, inflammatory processes and diseases like gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis and other soft tissue rheumatism. Examples of such genetic predispositions include but are not limited to the di-electcons 4 allele of apolipoprotein E, which increases the likelihood of Alzheimer's Disease; a loss of function or null mutation in the lipoprotein lipase gene coding region or promoter (e.g., mutations in the coding regions resulting in the substitutions D9N and N291S; for a review of genetic mutations in the lipoprotein lipase gene that increase the risk of cardiovascular diseases, dyslipidemias and dyslipoproteinemias (Hayden and Ma, 1992, *Mol. Cell. Biochem.* 113: 171 176); and familial combined hyperlipidemia and familial hypercholesterolemia.

In some embodiments, the compositions disclosed herein are provided to a subject as a preventative measure to a mammal having a non-genetic predisposition to cardiometabolic syndrome, in aging, Alzheimer's Disease, cancer, cardiovascular disease, diabetic nephropathy, diabetic retinopathy, a disorder of glucose metabolism, dyslipidemia, dyslipoproteinemia, enhancing bile production, enhancing reverse lipid transport, hypertension, impotence, inflammation, insulin resistance, lipid elimination in bile, modulating C-reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), a thrombotic disorder, inflammatory processes and diseases like gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis and other soft tissue rheumatism. Examples of such non-genetic predispositions include but are not limited to cardiac bypass surgery and percutaneous transluminal coronary angioplasty, which often lead to restenosis, an accelerated form of atherosclerosis; diabetes in women, which often leads to polycystic ovarian disease; and cardiovascular disease, which often leads to impotence. Accordingly, the compositions described herein can be used for the prevention of one disease or disorder and concurrently treating another disease (e.g., prevention of polycystic ovarian disease while treating diabetes; prevention of impotence while treating a cardiovascular disease).

In some embodiments, the compositions disclosed herein are provided to a subject to inhibit the onset of insulin resistance in a subject based on criteria including but not limited to family history, diet and drug use. In some embodiments, for example, an individual at risk for developing insulin resistance may believe it is in need or may self-identify or be identified based on family history, obesity, diabetes, CVD and other associated disease conditions including depression, mental health diseases or disorders, glucose and lipid metabolism disturbances, a diet high in fats, carbohydrates, low dietary fiber, deficiency of essential nutrients and not limited to drugs such as a statin drug, non-steroidal anti-inflammatory drug, steroid, oral contraceptive, hormone replacement therapy drug, beta blocker, potassium channel opener, or diuretic and depression drugs. Accordingly, some embodiments provide a method for inhibiting the development of drug-induced insulin resistance including administering a fast-acting, hydrophilic and a slow-acting, lipophilic chromium complex to an individual receiving a contemporaneous dose of a drug that induces insulin resistance. Advantageously, the amount of chromium complex administered is an amount effective to inhibit the development of insulin resistance.

The administration of an effective dose of a composition described herein (e.g. chromium histidinate and chromium picolinate), to subjects who have a diet or take drugs which have been linked with the onset of insulin resistance actually inhibits or attenuates the onset of insulin resistance. The supplementation with a fast-acting chromium and slow-acting complex, inhibits the induction of insulin resistance. By not developing insulin resistance in the first place, the patient is not exposed to the associated diseases and risks. The patient also does not need to take additional, and sometimes costly, medications to treat the insulin resistance and associated diseases.

Without being limited to a particular theory, we propose that combination chromium supplementation with fast and slow-acting chromium complex inhibits insulin resistance from developing by improving insulin sensitivity and lipid profile levels and lowering blood sugar. Accordingly, in one embodiment, a method of inhibiting or reducing the risk of insulin resistance through combination chromium supplementation is provided.

Chromium supplementation includes the administration of a fast-acting chromium complex such as histidinate in combination with at least one other slow-acting chromium complex to an individual. Advantageously, the fast and slow-acting chromium complexes are synthetic. The synthesis and use of chromium picolinates, for example, is described in U.S. Pat. Nos. Re 33,988 and 5,087,623, the entire contents of which are hereby incorporated herein by reference in their entirety. Chromic tripicolinate is available from health food stores, drug stores and other commercial sources. The synthesis and use of chromic polynicotinate is described in U.S. Pat. No. 5,194,615.

Inhibition of insulin resistance is accomplished by administering an effective dose of fast-acting chromium complex such as a chromium histidinate complex with a slow-acting chromium complex such as chromium picolinate to an individual separately or as a single composition. A subject can begin chromium supplementation at the beginning of their treatment with insulin-resistance. Alternatively, the subject can begin supplementation with a chromium complex after the subject's treatment with insulin-resistance has begun, but before developing insulin resistance.

Insulin resistance is a key pathogenic parameter of Type 2 diabetes, and clinical interventions that improve insulin sensitivity are considered cornerstones in the management of the disease. In addition, the relationship of insulin resistance to cardiovascular disease and its associated risk factors has been well established over the past few years. Therefore, in a preferred embodiment, methods and compositions for thwarting the development of insulin resistance are provided comprising the administration of a fast-acting and slow-acting chromium complexes with a hypoglycemic drug such as metformin, which inhibits insulin resistance from developing. Combinations of pharmacologic agents (such as sulfonylureas/metformin, sulfonylureas/glitazones, and metformin/glitazones) are highly effective pharmacologic interventions that appear to lower both glucose and insulin levels. Further, there is evidence that triple drug therapy (e.g. sulfonylureas/metformin/glitazones) can lower clinical glycemia in addition to lowering insulin levels. Hence, in some embodiments, compositions comprising a hydrophobic chromium complex and a hydrophilic chromium complex with metformin, sulfonylureas, and glitazones or combinations thereof are administered to a subject taking drugs which induce insulin resistance to inhibit the onset of such insulin resistance.

The disclosure represents the present technology in that the subject has a chance of developing insulin resistance or diabetes or associated conditions but not limited to cardiovascular disease, obesity, diabetes, combination one or two disease conditions based on ATPIII guidelines and or due to mental health conditions such as depression, schizophrenia, alzheimers disease and other conditions such HIV and HIV lipodystrophy and polycystic ovary syndrome. The insulin resistance might be due to family history, body weight, diet and drugs.

Treatment of Cardiovascular Diseases

The present invention provides methods for the treatment or prevention of a cardiovascular disease, comprising administering to a patient a therapeutically effective amount of a composition comprising, consisting essentially of, or consisting of chromium and histidine, or a chromium histidinate complex with a slow-acting chromium and a pharmaceutically acceptable vehicle. As used herein, the term "cardiovascular diseases" refers to diseases of the heart and circulatory system. These diseases are often associated with dyslipoproteinemias and/or dyslipidemias and/or familial hyperlipoproteinemias, hyper cholesterolemia and hyper lipidemia. Cardiovascular diseases which the compositions of the present invention are useful for preventing or treating include but are not limited to arteriosclerosis; atherosclerosis; stroke; ischemia; endothelium dysfunctions, in particular those dysfunctions affecting blood vessel elasticity; peripheral vascular disease; coronary heart disease; myocardial infarction; cerebral infarction and restenosis.

The compositions disclosed herein, e.g. a fast-acting chromium such as chromium histidinate with a slow-acting chromium complexes, e.g. chromium picolinate, are preferably used in methods for treating cardiovascular disease and its related pathologies, including, for example, hypertrophy, hypertension, congestive heart failure, myocardial ischemia, ischemia reperfusion injuries in an organ, arrhythmia, and myocardial infarction. One embodiment is directed to a method of treating cardiovascular disease in a mammal by concurrently administering to the mammal a therapeutically effective amount of a therapeutic cardiovascular compound, and a hydrophilic chromium complex and a lipophilic chromium complex. Therapeutic cardiovascular compounds suitable for use in methods described herein include an angiotensin converting enzyme inhibitor, an angiotensin II receptor antagonist, a calcium channel blocker, an anti-thrombotic agent, a β-adrenergic receptor antagonist, a vasodilator, a diuretic, an α-adrenergic receptor antagonist, an antioxidant, and a mixture thereof. In some embodiments, the therapeutic cardiovascular compound is PPADS.

Treatment of Dyslipidemias

Also provided are methods for the treatment or prevention of a dyslipidemia comprising administering to a patient a therapeutically effective amount of composition disclosed herein, i.e., a fast-acting hydrophilic chromium complex in combination with a slow-acting or lipophilic chromium complex, e.g. chromium histidinate complex, a chromium picolinate complex, and a pharmaceutically acceptable vehicle.

As used herein, the term "dyslipidemias" refers to disorders that lead to or are manifested by aberrant levels of circulating lipids. To the extent that levels of lipids in the blood are too high, the compositions described herein are administered to a patient to restore normal levels. Normal levels of lipids are reported in medical treatises known to those of skill in the art. For example, recommended blood levels of LDL, HDL, free triglycerides and others parameters relating to lipid metabolism can be found at the web site of the American Heart Association and that of the National Cholesterol Education Program of the National Heart, Lung and Blood Institute (http://www.americanheart.org/cholesterol/about_level.html and http://www.nhlbi.nih.gov/health/public/heart/chol/hbc_what.html, respectively). At the present time, the recommended level of HDL cholesterol in the blood is above 35 mg/dL; the recommended level of LDL cholesterol in the blood is below 70 mg/dL if they have multiple risk factors; the recommended LDL:HDL cholesterol ratio in the blood is below 5:1, ideally 3.5:1; and the recommended level of free triglycerides in the blood is less than 200 mg/dL.

Dyslipidemias which the compositions of the present invention are useful for preventing or treating hyperlipidemia and low blood levels of high density lipoprotein (HDL) cholesterol. In certain embodiments, the hyperlipidemia for prevention or treatment by the compounds of the present invention is familial hypercholesterolemia; familial combined hyperlipidemia; reduced or deficient lipoprotein lipase levels or activity, including reductions or deficiencies resulting from lipoprotein lipase mutations; hypertriglyceridemia; hypercholesterolemia; high blood levels of urea bodies (e.g. .beta.-OH butyric acid); high blood levels of Lp(a) cholesterol; high blood levels of low density lipoprotein (LDL) cholesterol; high blood levels of very low density lipoprotein (VLDL) cholesterol and high blood levels of non-esterified fatty acids.

The present invention further provides methods for altering lipid metabolism in a patient, e.g., reducing LDL in the blood of a patient, reducing free triglycerides in the blood of a patient, increasing the ratio of HDL to LDL in the blood of a patient, and inhibiting saponified and/or non-saponified fatty acid synthesis, said methods comprising administering to the patient a compound or a composition comprising a fast-acting chromium complex and a slow-acting chromium complex in an amount effective alter lipid metabolism.

Treatment of Dyslipoproteinemias

Also provided are methods for the treatment or prevention of a dyslipoproteinemia comprising administering to a patient a therapeutically effective amount of a composition comprising a fast-acting chromium complex, a slow-acting chromium complex, and a therapeutically/nutritionally acceptable vehicle.

As used herein, the term "dyslipoproteinemias" refers to disorders that lead to or are manifested by aberrant levels of circulating lipoproteins. To the extent that levels of lipoproteins in the blood are too high, the compositions described herein are administered to a patient to restore normal levels. Conversely, to the extent that levels of lipoproteins in the blood are too low, the compositions described herein are administered to a patient to restore normal levels. Normal levels of lipoproteins are reported in medical treatises known to those of skill in the art.

Dyslipoproteinemias which the compositions of the present invention are useful for preventing or treating include but are not limited to high blood levels of LDL; high blood levels of apolipoprotein B (apo B); high blood levels of Lp(a); high blood levels of apo(a); high blood levels of VLDL; low blood levels of HDL; reduced or deficient lipoprotein lipase levels or activity, including reductions or deficiencies resulting from lipoprotein lipase mutations; hypoalphalipoproteinemia; lipoprotein abnormalities associated with diabetes; lipoprotein abnormalities associated with obesity; lipoprotein abnormalities associated with Alzheimer's Disease; and familial combined hyperlipidemia.

Further provided are methods for reducing apo C-II levels in the blood of a patient; reducing apo C-III levels in the blood of a patient; elevating the levels of HDL associated proteins, including but not limited to apo A-I, apo A-II, apo A-IV and apo E in the blood of a patient; elevating the levels of apo E in the blood of a patient, and promoting clearance of triglycerides from the blood of a patient, said methods comprising administering to the patient a fast-acting chromium complex and a slow-acting chromium complex in an amount effective to bring about said reduction, elevation or promotion, respectively.

Treatment of Glucose Metabolism Disorders

Also provided are methods for the treatment or prevention of a glucose metabolism disorder, comprising providing to a subject with or at risk of developing a glucose metabolism disorder a therapeutically effective amount of a fast-acting chromium complex and slow-acting chromium complex and a pharmaceutically acceptable vehicle. As used herein, the term "glucose metabolism disorders" refers to disorders that lead to or are manifested by aberrant glucose storage and/or utilization. To the extent that indicia of glucose metabolism (i.e., blood insulin, blood glucose) are too high, the compositions described herein are administered to a patient to restore normal levels. Conversely, to the extent that indicia of glucose metabolism are too low, the compositions described herein are administered to a patient to restore normal levels. Normal indicia of glucose metabolism are reported in medical treatises known to those of skill in the art.

Glucose metabolism disorders which the compositions of the present invention are useful for preventing or treating include but are not limited to impaired glucose tolerance; insulin resistance; insulin resistance related breast, colon or prostate cancer; diabetes, including but not limited to type 2 diabetes, type 1 diabetes, gestational diabetes mellitus (GDM), and maturity onset diabetes of the young (MODY); pancreatitis; hypertension; polycystic ovarian disease; HIV lipodystrophy, hormonal imbalance, hypercotisol levers, endothelial dysfunction, Alzheimer's disease, aging and high levels of blood insulin and/or glucose.

Further provided are methods for altering glucose metabolism in a patient, for example to increase insulin sensitivity and/or oxygen consumption of a patient, said methods comprising administering to the mammal a compound or a composition comprising a fast-acting or hydrophilic chromium complex in combination with a slow-acting or lipophilic chromium complex, in an amount effective to alter glucose metabolism.

Treatment of PPAR-Associated Disorders

Also provided are methods for the treatment or prevention of a PPAR-associated disorder, comprising administering to a patient a therapeutically effective amount of a lipophilic chromium complex and a hydrophilic chromium complex (e.g. chromium histidinate) and a pharmaceutically acceptable vehicle. As used herein, "treatment or prevention of PPAR associated disorders" encompasses treatment or prevention of rheumatoid arthritis; multiple sclerosis; psoriasis; inflammatory bowel diseases; breast; colon or prostate cancer; low levels of blood HDL; low levels of blood, lymph and/or cerebrospinal fluid apo E; low blood, lymph and/or cerebrospinal fluid levels of apo A-I; high levels of blood VLDL; high levels of blood LDL; high levels of blood triglyceride; high levels of blood apo B; high levels of blood apo C-III and reduced ratio of post-heparin hepatic lipase to lipoprotein lipase activity. HDL can be elevated in lymph and/or cerebral fluid.

Treatment of Renal Diseases

Further provided are methods for the treatment or prevention of a renal disease, comprising administering to a patient a therapeutically effective amount of a composition comprising a fast-acting chromium complex and a slow-acting chromium complex and a pharmaceutically acceptable vehicle. Renal diseases that can be treated by the compounds of the present invention include glomerular diseases (including but not limited to acute and chronic glomerulonephritis, rapidly progressive glomerulonephritis, nephrotic syndrome, focal proliferative glomerulonephritis, glomerular lesions associated with systemic disease, such as systemic lupus erythematosus, Goodpasture's syndrome, multiple myeloma, diabetes, neoplasia, sickle cell disease, and chronic inflammatory diseases), tubular diseases (including but not limited to acute tubular necrosis and acute renal failure, polycystic renal diseasemedullary sponge kidney, medullary cystic disease, nephrogenic diabetes, and renal tubular acidosis), tubulointerstitial diseases (including but not limited to pyelonephritis, drug and toxin induced tubulointerstitial nephritis, hypercalcemic nephropathy, and hypokalemic nephropathy) acute and rapidly progressive renal failure, chronic renal failure, nephrolithiasis, or tumors (including but not limited to renal cell carcinoma and nephroblastoma). In a most preferred embodiment, renal diseases that are treated by the compounds of the present invention are vascular diseases, including but not limited to hypertension, nephrosclerosis, microangiopathic hemolytic anemia, atheroembolic renal disease, diffuse cortical necrosis, and renal infarcts.

Treatment of Cancer

Provided herein are methods for the treatment or prevention of cancer, comprising administering to a patient a therapeutically effective amount of a composition comprising a fast-acting chromium complex such as chromium histidinate, a slow-acting chromium complex such as chromium picolinate, and a pharmaceutically acceptable vehicle. Types of cancer that can be treated using combination chromium supplementation include, but are not limited to solid tumors, including but not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophogeal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas cystadenocarcinoma, medullary carcinoma, bronchogenic carcinoma, renal cell carcinoma, hepatoma bile duct carcinoma choriocarcinoma seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme astrocytoma medulloblastoma, craniopharyngioma, ependymoma, pinealoma, hemangioblastoma acoustic neuroma, oligodendroglioma, meningioma, skin cancer, melanoma, neuroblastoma, retinoblastoma, Blood-borne cancers, including but not limited to: acute lymphoblastic B-cell leukemia, acute lymphoblastic T-cell leukemia, acute myeloblastic leukemia, "AML," acute promyelocytic leukemia "APL," acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia, "CML," chronic lymphocytic leukemia, "CLL," hairy cell leukemia, multiple myeloma Acute and chronic leukemias, Lymphoblastic myelogenous leukemias, lymphocytic myelocytic leukemias, Lymphomas: such as Hodgkin's disease, non-Hodgkin's Lymphoma, Multiple myeloma, Waldenstrom's macroglobulinemia, Heavy chain disease, and Polycythemia vera.

Cancer, including, but not limited to, a tumor, metastasis, or any disease or disorder characterized by uncontrolled cell growth, can be treated or prevented by combination chromium supplementation as described herein.

Treatment of Other Diseases

Also provided herein are methods for the treatment or prevention of Alzheimer's Disease, Syndrome X, septicemia, thrombotic disorders, obesity, pancreatitis, hypertension, inflammation, and impotence, comprising administering to a patient a therapeutically effective amount of a composition comprising, consisting essentially of, or consisting of a fast-acting chromium complex, a slow-acting chromium complex, and a nutritionally acceptable vehicle.

As used herein, "treatment or prevention of Alzheimer's Disease" encompasses treatment or prevention of lipoprotein abnormalities associated with Alzheimer's Disease.

As used herein, "treatment or prevention of Syndrome X or Metabolic Syndrome" encompasses treatment or prevention of a symptom thereof, including but not limited to impaired glucose tolerance, hypertension and dyslipidemia/dyslipoproteinemia.

As used herein, "treatment or prevention of septicemia" encompasses treatment or prevention of septic shock.

As used herein, "treatment or prevention of thrombotic disorders" encompasses treatment or prevention of high blood levels of fibrinogen and promotion of fibrinolysis.

In addition to treating or preventing obesity, the compositions described herein can be administered to an individual to promote weight reduction of the individual.

As used herein, "treatment or prevention of diabetic nephropathy" encompasses treating or preventing kidney disease that develops as a result of diabetes mellitus (DM). Diabetes mellitus is a disorder in which the body is unable to metabolize carbohydrates (e.g., food starches, sugars, cellulose) properly. The disease is characterized by excessive amounts of sugar in the blood (hyperglycemia) and urine; inadequate production and/or utilization of insulin; and by thirst, hunger, and loss of weight. Thus, the compositions disclosed herein can also be used to treat or prevent diabetes mellitus.

As used herein, "treatment or prevention of diabetic retinopathy" encompasses treating or preventing complications of diabetes that lead to or cause blindness. Diabetic retinopathy occurs when diabetes damages the tiny blood vessels inside the retina, the light-sensitive tissue at the back of the eye.

As used herein, "treatment or prevention of impotence" includes treating or preventing erectile dysfunction, which encompasses the repeated inability to get or keep an erection firm enough for sexual intercourse. The word "impotence" can also be used to describe other problems that interfere with sexual intercourse and reproduction, such as lack of sexual desire and problems with ejaculation or orgasm. The term "treatment or prevention of impotence" includes, but is not limited to impotence that results as a result of damage to nerves, arteries, smooth muscles, and fibrous tissues, or as a result of disease, such as, but not limited to, diabetes, kidney disease, chronic alcoholism, multiple sclerosis, atherosclerosis, vascular disease, and neurologic disease.

As used herein, "treatment or prevention of hypertension" encompasses treating or preventing blood flow through the vessels at a greater than normal force, which strains the heart; harms the arteries; and increases the risk of heart attack, stroke, and kidney problems. The term hypertension includes, but is not limited to, cardiovascular disease, essential hypertension, hyperpiesia, hyperpiesis, malignant hypertension, secondary hypertension, or white-coat hypertension.

As used herein, "treatment or prevention of inflammation" encompasses treating or preventing inflammation diseases including, but not limited to, chronic inflammatory disorders of the joints including arthritis, e.g., rheumatoid arthritis and osteoarthritis; respiratory distress syndrome, inflammatory bowel diseases such as ileitis, ulcerative colitis and Crohn's disease; and inflammatory lung disorders such as asthma and chronic obstructive airway disease, inflammatory disorders of the eye such as corneal dystrophy, trachoma, onchocerciasis, uveitis, sympathetic ophthalmitis, and endophthalmitis; inflammatory disorders of the gum, e.g., periodontitis and gingivitis; tuberculosis; leprosy; inflammatory diseases of the kidney including glomerulonephritis and nephrosis; inflammatory disorders of the skin including acne, sclerodermatitis, psoriasis, eczema, photoaging and wrinkles; inflammatory diseases of the central nervous system, including AIDS-related neurodegeneration, stroke, neurotrauma, Alzheimer's disease, encephalomyelitis and viral or autoimmune encephalitis; autoimmune diseases including immune-complex vasculitis, systemic lupus and erythematodes; systemic lupus erythematosus (SLE); and inflammatory diseases of the heart such as cardiomyopathy.

Combination Therapy

In certain embodiments, the compounds and compositions disclosed herein can be used in combination therapy with at least one other therapeutic agent. The combination chromium supplementation described herein (e.g., a fast-acting chromium complex and a slow-acting chromium complex) and the therapeutic agent can act additively or, more preferably, synergistically. In a preferred embodiment, combination chromium supplementation described herein is administered concurrently with the administration of another therapeutic agent, which can be part of the same combination chromium supplementation described herein or a different composition. In another embodiment, both a hydrophilic chromium complex and a lipophilic chromium complex are administered prior or subsequent to administration of another therapeutic agent. As many of the disorders for which the compositions described herein are useful in treating are chronic disorders, in one embodiment combination therapy involves alternating between administering a combination chromium supplementation and a composition comprising another therapeutic agent, e.g., to minimize the toxicity associated with a particular drug. The duration of administration of each drug or therapeutic agent can be, e.g., one month, three months, six months, or a year. In certain embodiments, when a composition described herein is administered concurrently with another therapeutic agent that potentially produces adverse side effects including but not limited to toxicity, the therapeutic agent can advantageously be administered at a dose that falls below the threshold at which the adverse side is elicited. The standard dosage for the compounds discussed below are known to those skilled in the art.

The combination chromium supplementation can be administered together with a statin. Statins for use in combination with the compounds and compositions described herein include but are not limited to atorvastatin, pravastatin, fluvastatin, lovastatin, simvastatin, and cerivastatin.

The combination chromium supplementation can also be administered together with a PPAR agonist, for example a thiazolidinedione or a fibrate. Thiazolidinediones for use in combination with the compounds and compositions described herein include but are not limited to 5 ((4 (2(methyl 2 pyridinylamino)ethoxy)phenyl)methyl) 2,4 thiazolidinedione, troglitazone, pioglitazone, ciglitazone, WAY 120,744, englitazone, AD 5075, darglitazone, and rosiglitazone. Fibrates for use in combination with the compounds and compositions described herein include but are not limited to gemfibrozil, fenofibrate, clofibrate, or ciprofibrate. As mentioned previously, a therapeutically effective amount of a fibrate or thiazolidinedione often has toxic side effects. Accordingly, in a preferred embodiment of the present invention, when a combination chromium supplementation is administered in combination with a PPAR agonist, the dosage of the PPAR agonist is below that which is accompanied by toxic side effects.

The combination chromium supplementation can also be administered together with a bile acid binding resin. Bile acid binding resins for use in combination with the compounds and compositions described herein include but are not limited to cholestyramine and colestipol hydrochloride. The present compositions can also be administered together with niacin or nicotinic acid. The present compositions can also be administered together with a RXR agonist. RXR agonists for use in combination with the compositions disclosed herein include but are not limited to LG 100268, LGD 1069, 9-cis retinoic acid, 2 (1(3,5,5,8,8 pentamethyl 5,6,7,8 tetrahydro 2 naphthyl)cyclopropyl) pyridine 5 carboxylic acid, or 4 ((3,5,5,8,8 pentamethyl 5,6,7,8 tetrahydro 2 naphthyl)2 carbonyl) benzoic acid. The combination chromium supplementation can also be administered together with an anti-obesity drug. Anti-obesity drugs for use in combination with the combination chromium supplementation disclosed herein include but are not limited to β.-adrenergic receptor agonists, preferably β.-3 receptor agonists, fenfluramine, dexfenfluramine, sibutramine, bupropion, fluoxetine, and phentermine. The combination chromium supplementation can also be administered together with a hormone. Hormones for use in combination with the compositions disclosed herein include but are not limited to thyroid hormone, estrogen and insulin. Preferred insulins include but are not limited to injectable insulin, transdermal insulin, inhaled insulin, or any combination thereof. As an alternative to insulin, an insulin derivative, secretagogue, sensitizer or mimetic can be used. Insulin secretagogues for use in combination with the combination chromium supplementation disclosed herein include but are not limited to forskolin, dibutryl cAMP or isobutylmethylxanthine (IBMX).

The combination chromium supplementation can also be administered together with a phosphodiesterase type 5 ("PDE5") inhibitor to treat or prevent disorders, such as but not limited to, impotence. In a particular, embodiment the combination is a synergistic combination of a combination chromium supplementation and a PDE5 inhibitor.

The present compositions can also be administered together with a tyrophostine or an analog thereof. Tyrophostines for use in combination with the combination chromium supplementation include but are not limited to tryophostine 51.

The present compositions can also be administered together with sulfonylurea-based drugs. Sulfonylurea-based drugs for use in combination chromium supplementation disclosed herein include, but are not limited to, glisoxepid, glyburide, acetohexamide, chlorpropamide, glibornuride, tolbutamide, tolazamide, glipizide, gliclazide, gliquidone, glyhexamide, phenbutamide, and tolcyclamide. The combination chromium supplementation can also be administered together with a biguanide. Biguanides for use in combination with the compositions disclosed herein include but are not limited to metformin, phenformin and buformin.

The combination chromium supplementation can also be administered together with an α-glucosidase inhibitor. α-glucosidase inhibitors for use in combination with the combination chromium supplementation include but are not limited to acarbose and miglitol.

The combination chromium supplementation can also be administered together with an apo A-I agonist. In one embodiment, the apo A-I agonist is the Milano form of apo A-I (apo A-IM). In a preferred mode of the embodiment, the apo A-IM for administration in conjunction with the combination chromium supplementation is produced by the method of U.S. Pat. No. 5,721,114 to Abrahamsen. In a more preferred embodiment, the apo A-I agonist is a peptide agonist.

In a preferred mode of the embodiment, the apo A-I peptide agonist for administration in conjunction with the combination chromium supplementaiton is a peptide of U.S. Pat. No. 6,004,925 or 6,037,323 to Dasseux.

The combination chromium supplementation can also be administered together with apolipoprotein E (apo E).

In yet other embodiments, the combination chromium supplementation can be administered together with an HDL-raising drug; an HDL enhancer; or a regulator of the apolipoprotein A-I, apolipoprotein A-IV and/or apolipoprotein genes.

In one embodiment, the other therapeutic agent can be an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethyleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine and tropisetron.

In another embodiment, the other therapeutic agent can be an hematopoietic colony stimulating factor. Suitable hematopoietic colony stimulating factors include, but are not limited to, filgrastim, sargramostim, molgramostim and erythropoietin α.

In still another embodiment, the other therapeutic agent can be an opioid or non-opioid analgesic agent. Suitable opioid analgesic agents include, but are not limited to, morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam and sulindac.

Combination Therapy of Cardiovascular Diseases

The combination chromium supplementation (e.g., slow-acting chromium complex and fast-acting chromium complex) can be administered together with a known cardiovascular drug. Cardiovascular drugs for use in combination with the combination chromium supplementation to prevent or treat cardiovascular diseases include but are not limited to peripheral antiadrenergic drugs, centrally acting antihypertensive drugs (e.g., methyldopa, methyldopa HCl), antihypertensive direct vasodilators (e.g., diazoxide, hydralazine HCl), drugs affecting renin-angiotensin system, peripheral vasodilators, phentolamine, antianginal drugs, cardiac glycosides, inodilators (e.g., aminone, milrinone, enoximone, fenoximone, imazodan, sulmazole), antidysrhythmic drugs, calcium entry blockers, ranitine, bosentan, and rezulin.

Surgical Uses

Cardiovascular diseases such as atherosclerosis often require surgical procedures such as angioplasty. Angioplasty is often accompanied by the placement of a reinforcing a metallic tube shaped structure known as a "stent" into a damaged coronary artery. For more serious conditions, open heart surgery such as coronary bypass surgery may be required. These surgical procedures entail using invasive surgical devices and/or implants, and are associated with a high risk of restenosis and thrombosis. Accordingly, the combination chromium supplementation described herein (i.e., a lipophilic chromium complex and a hydrophilic chromium complex) can be used as coatings on surgical devices (e.g., catheters) and implants (e.g., stents) to reduce the risk of restenosis and thrombosis associated with invasive procedures used in the treatment of cardiovascular diseases.

Veterinary and Livestock Uses

The combination chromium supplementation (i.e., a lipophilic chromium complex and a hydrophilic chromium complex) can be administered to an animal or non-human animal for a veterinary use for treating or preventing a disease or disorder disclosed herein.

In a specific embodiment, the non-human animal is a household pet. In another specific embodiment, the non-human animal is a livestock animal. In a preferred embodiment, the non-human animal is a mammal, most preferably a cow, horse, sheep, pig, cat, dog, mouse, rat, rabbit, or guinea pig. In another preferred embodiment, the non-human animal is a fowl species, most preferably a chicken, turkey, duck, goose, or quail.

In addition to veterinary uses, the combination chromium supplementation disclosed herein can be used to reduce the fat content of livestock to produce leaner meats. Alternatively, the combination chromium supplementation disclosed herein can be used to reduce the cholesterol content of eggs by administering the compounds to a chicken, quail, or duck hen. For non-human animal uses, the compositions disclosed herein can be administered via the animals' feed or orally as a drench composition.

Therapeutic/Prophylactic Administration and Compositions

Due to the activity of the combination chromium supplementation described herein, they are useful in veterinary and human medicine. As described above, the combination chromium supplementation described herein are useful for the treatment or prevention of cardiometabolic syndrome, aging, Alzheimer's Disease, cancer, cardiovascular disease, diabetic nephropathy, diabetic retinopathy, a disorder of glucose metabolism, dyslipidemia, dyslipoproteinemia, hypertension, impotence, inflammation, insulin resistance, lipid elimination in bile, modulating C reactive protein, obesity, oxysterol elimination in bile, pancreatitis, Parkinson's disease, a peroxisome proliferator activated receptor-associated disorder, phospholipid elimination in bile, renal disease, septicemia, metabolic syndrome disorders (e.g., Syndrome X), a thrombotic disorder, enhancing bile production, -enhancing reverse lipid transport, inflammatory processes and diseases like gastrointestinal disease, irritable bowel syndrome (IBS), inflammatory bowel disease (e.g., Crohn's Disease, ulcerative colitis), arthritis (e.g., rheumatoid arthritis, osteoarthritis), autoimmune disease (e.g., systemic lupus erythematosus), scleroderma, ankylosing spondylitis, gout and pseudogout, muscle pain: polymyositis/polymyalgia rheumatica/fibrositis; infection and arthritis, juvenile rheumatoid arthritis, tendonitis, bursitis and other soft tissue rheumatism.

Provided herein are methods of treatment and prophylaxis of the conditions enumerated above by providing to a subject of a therapeutically effective amount of a fast-acting chromium complex and a slow-acting chromium complex as disclosed herein. In the various embodiments disclosed herein, the subject can be a mammal such as an animal, including, but not limited to, an animal such a cow, horse, sheep, pig, chicken, turkey, quail, cat, dog, mouse, rat, rabbit, guinea pig, etc., and most preferably a human.

The combination chromium supplementation disclosed herein is useful for methods for treating diabetes and its related pathologies, cardiovascular and related diseases, such as, for example, diabetes retinopathy, diabetes nephropathy, diabetes neuropathy, diabetes foot problems, diabetes infections and inflammations, diabetes with cardiovascular complications such as hypertrophy, hypertension, congestive heart failure, myocardial ischemia, ischemia reperfusion injuries in an organ, arrhythmia, and myocardial infarction. One embodiment is directed to a method of treating cardiovascular disease in a mammal by concurrently administering to the mammal a therapeutically effective amount of a combination chromium supplementation described herein (e.g. a lipophilic chromium complex and a hydrophilic chromium complex) and a therapeutic cardiovascular compound such as chromium histidine or chromium complex. Therapeutic cardiovascular compounds suitable for use in methods described herein include an angiotensin converting enzyme inhibitor, an angiotensin II receptor antagonist, a calcium channel blocker, an anti-thrombotic agent, a β-adrenergic receptor antagonist, a vasodilator, a diuretic, an α-adrenergic receptor antagonist, an antioxidant, and a mixture thereof.

The combination chromium supplementation disclosed herein is useful for the methods for treating obesity and related pathologies, obesity related to complications such as diabetes, diabetes risk factors, leptin resistance, abdominal fat distribution, cardiovascular disease and its related pathologies, cardiovascular and related diseases, such as, for example, hypertrophy, hypertension, congestive heart failure, myocardial ischemia, ischemia reperfusion injuries in an organ, arrhythmia, and myocardial infarction. One embodiment is directed to a method of treating obesity and its associated complications such as diabetes, cardiovascular disease and insulin resistance in a mammal by concurrently administering to the mammal a therapeutically effective amount of a combination chromium supplementation (e.g. a lipophilic chromium complex and a hydrophilic chromium complex) and a therapeutic cardiovascular compound. Therapeutic cardiovascular compounds can include but are not limited to an angiotensin converting enzyme inhibitor, an angiotensin II receptor antagonist, a calcium channel blocker, an anti-thrombotic agent, a β-adrenergic receptor antagonist, a vasodilator, a diuretic, an α-adrenergic receptor antagonist, an antioxidant, antihyperglycemic drugs, insulin, antiobesity drugs, antidepressants etc. and a mixture thereof.

The present invention is further disclosed in the following Examples, which are provided for illustrative purposes and are not in any way intended to limit the scope of the invention as claimed.

Example 1

Combination Chromium Picolinate/Chromium Histidinate Improves Glucose Uptake In Vitro The following example describes experiments that compared the effects of chromium supplementation in the form of chromium picolinate versus a combination of chromium picolinate:chormium histidinate (1:1 elemental chromium) on glucose uptake in skeletal muscle cells. The amounts of chromium picolinate and the combination were adjusted so as to provide equimolar amounts of elemental chromium. For the combination, 50% of the elemental chromium was provided in the form of chromium picolinate, and 50% was provided in the form of chromium histidinate. To assess glucose uptake, [$^3$H]C-deoxyglucose was added to cultures of skeletal muscle, in media with or without insulin and with or without the indicated chromium supplementation. Uptake of the labeled glucose by the cells was calculated.

FIG. 1 shows the percent increase in glucose uptake in cultures receiving chromium supplementation over cultures without chromium supplementation, in the presence and absence of insulin. Both chromium picolinate and the combination chromium picolinate/chromium histidinate stimulated glucose uptake in insulin-stimulated cells. The combination enhanced glucose uptake in both basal and insulin-stimulated cultures to a greater extent than chromium picolinate, even though the cultures were treated with equivalent amounts of elemental chromium.

Example 2

Combination Chromium Picolinate/Chromium Histidinate Synergistically Improves Glucose Levels, Cholesterol Levels, Triglyceride Levels and Free Fatty Acid Levels In Vivo The following example describes a series of experiments that compared the effects of chromium supplementation in the form of chromium picolinate, chromium histidinate, and a combination of chromium picolinate/chromium histidinate on various metabolic functions in rats fed normal and high fat diets.

Wistar rats were reared at the temperature of (22±2° C.), humidity (55±5%) and a 12/12 h light/dark cycle. Pellet food and water were provided ad libitum.

Rats were randomly assigned to one of eight treatment groups.

Group 1: Control rats were fed standard diet (12% of calories as fat) for 12 weeks.

Group 2: Rats were fed standard diet with chromium picolinate (14.3 µg, providing 1.43 µg chromium) included in the water for 12 weeks.

Group 3: Rats were fed standard diet with chromium histidinate (19.7 µg, providing 1.43 µg chromium) included in the water for 12 weeks.

Group 4: Rats were fed standard diet with chromium picolinate (7.15 µg) and chromium histidinate (9.85 µg), providing 1.43 µg total chromium in the water for 12 weeks.

Group 5: Rats were fed high fat diet (40% of calories as fat) for 12 weeks.

Group 6: Rats were fed high-fat diet (40% of calories as fat) and with chromium picolinate (14.3 µg, providing 1.43 µg chromium) included in the water for 12 weeks.

Group 7: Rats were fed high-fat diet (40% of calories as fat) and with chromium histidinate (19.7 µg, providing 1.43 µg chromium) included in the water for 12 weeks.

Group 8: Rats were fed high-fat diet (40% of calories as fat) and with chromium picolinate (7.15 µg) and chromium histidinate (9.85 µg), providing 1.43 µg total chromium in the water for 12 weeks.

Bodyweight, serum glucose, composite insulin sensitivity index (CISI), serum cholesterol, serum triglycerides and serum free fatty acid levels were measured. The baseline levels for the control rats (no chromium supplementation) that were fed normal or high fat diets are shown in Table 1, below.

TABLE 1

|  | Normal Rats | High Fat Diet Rats |
| --- | --- | --- |
| Body weight (g) | 277 | 317 |
| Serum glucose (mg/dL) | 100 | 130 |
| CISI (mg/dL) | 2.7 | 1.6 |
| Serum cholesterol (mg/dL) | 58 | 112 |
| Serum triglycerides (mg/dL) | 46 | 107 |
| Free fatty acids (mmol/L) | 1.4 | 3.1 |

Serum glucose levels, serum cholesterol levels, serum triglyceride levels, and free fatty acid levels were measured in all groups after twelve weeks. The data are presented in FIGS. 2A-5B.

Figures 2A, 2B:
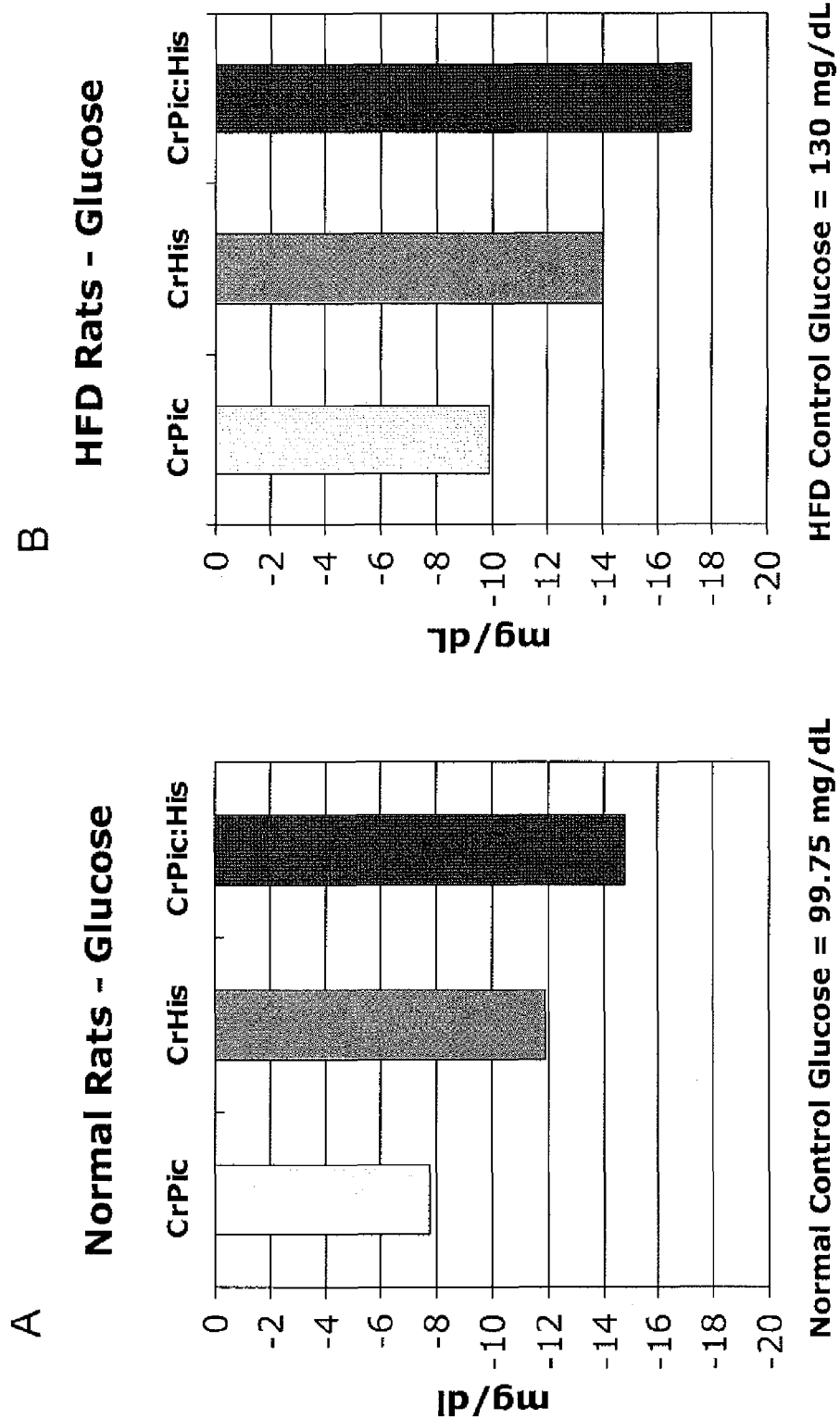
FIGS. 2A and 2B are bar graphs showing the change in serum glucose levels (mg/dL) in rats fed either a normal diet (16A) or a high fat diet (16B), supplemented with chromium picolinate (CrPic), chromium histidinate (CrHis), or a combination of chromium picolinate/chromium histidinate (CrPic:His) relative to rats that did not receive chromium supplementation.

Chromium histidinate decreased serum glucose levels in both normal and high-fat fed rats to a significantly greater degree than chromium picolinate. Surprisingly, the treatment group that received chromium picolinate/chromium histidinate (in the same total amount of elemental chromium as provided by chromium picolinate or chromium histidinate alone) exhibited a significantly greater reduction in serum glucose levels than the treatment groups that received chromium supplementation in the form of chromium as chromium picolinate or chromium histidinate alone. FIGS. 2A and 2B. The synergistic effect of the combination could not have been predicted.

Figures 3A, 3B:
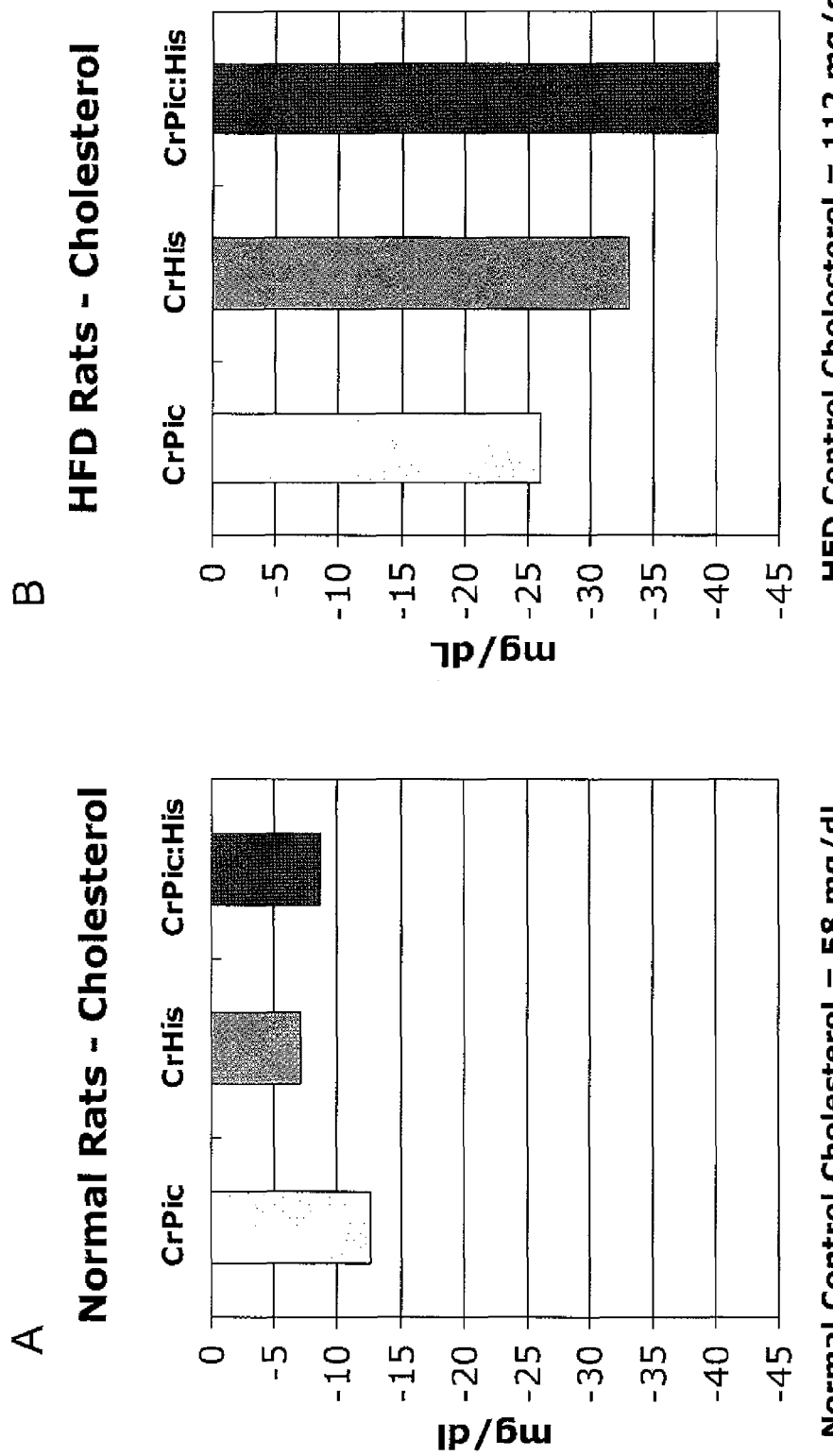
FIGS. 3A and 3B are bar graphs showing the change in serum cholesterol levels (mg/dL) in rats fed either a normal diet (17A) or a high fat diet (17B), supplemented with chromium picolinate (CrPic), chromium histidinate (CrHis), or a combination of chromium picolinate/chromium histidinate (CrPic:His) relative to rats that did not receive chromium supplementation.

Chromium picolinate, chromium histidinate and the combination of chromium picolinate/chromium histidinate resulted in a significant decrease in total serum cholesterol levels in rats fed a normal diet. FIG. 3A. Surprisingly, the treatment group that received chromium picolinate/chromium histidinate (in the same total amount of elemental chromium as provided by chromium picolinate or chromium histidinate alone) had significantly lower serum cholesterol levels than the treatment groups that received chromium supplementation in the form of chromium as chromium picolinate or chromium histidinate alone. FIG. 3B. The synergistic effect of the combination could not have been predicted.

Figure 4A:
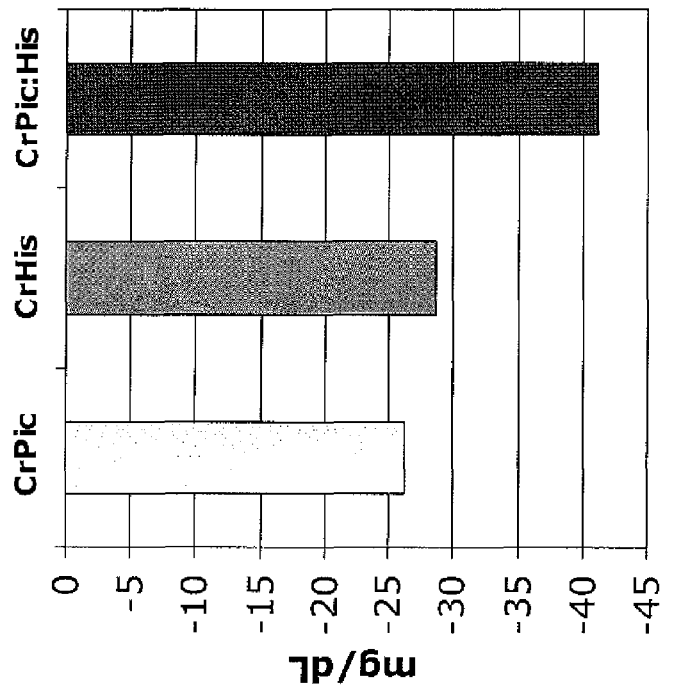
FIGS. 4A and 4B are bar graphs showing the change in serum triglyceride levels (mg/dL) in rats fed either a normal diet (18A) or a high fat diet (18B), supplemented with chromium picolinate (CrPic), chromium histidinate (CrHis), or a combination of chromium picolinate/chromium histidinate (CrPic:His) relative to rats that did not receive chromium supplementation.
Figure 4B:
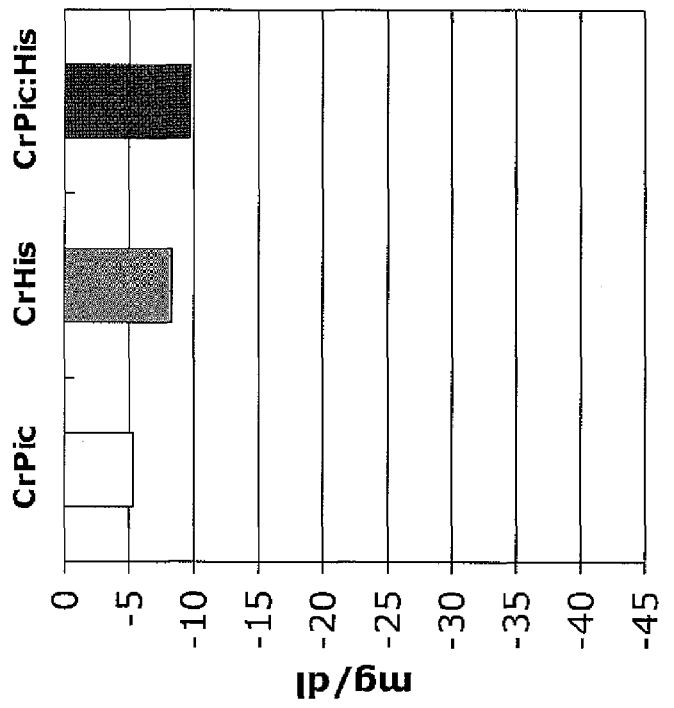

Chromium picolinate, chromium histidinate and the combination of chromium picolinate/chromium histidinate resulted in a significant decrease in serum triglyceride levels in rats fed a normal or high fat diet. FIGS. 4A and 4B. Surprisingly, the treatment group that received chromium picolinate/chromium histidinate (in the same total amount of elemental chromium as provided by chromium picolinate or chromium histidinate alone) had significantly lower serum triglyceride levels than the treatment groups that received chromium supplementation in the form of chromium as chromium picolinate or chromium histidinate alone. FIG. 4B. The synergistic effect of the combination could not have been predicted.

Figures 5A, 5B:
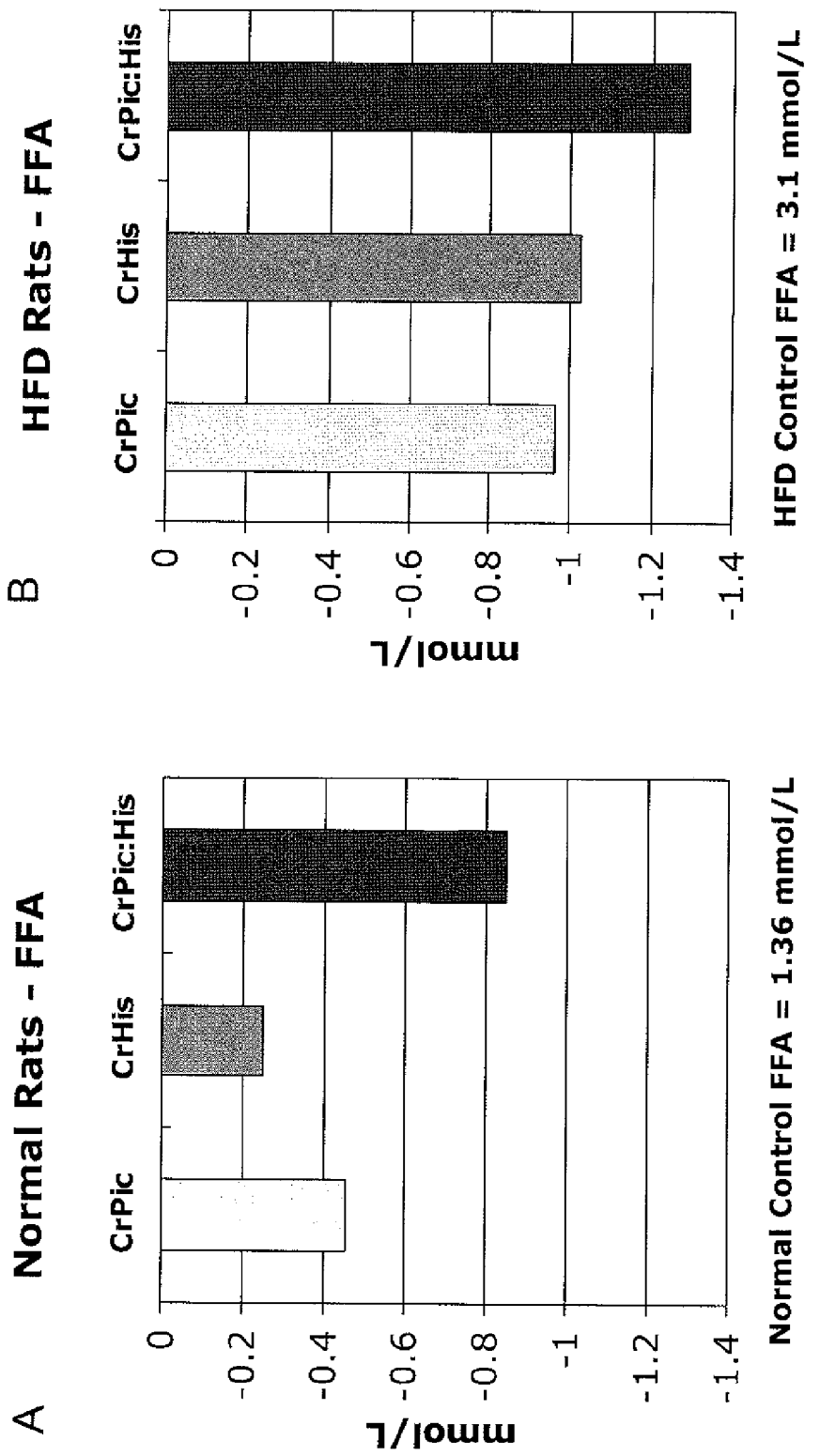
FIGS. 5A and 5B are bar graphs showing the change in free fatty acid levels (mmol/L) in rats fed either a normal diet (18A) or a high fat diet (18B), supplemented with chromium picolinate (CrPic), chromium histidinate (CrHis), or a combination of chromium picolinate/chromium histidinate (CrPic:His) relative to rats that did not receive chromium supplementation.

Chromium picolinate, chromium histidinate and the combination of chromium picolinate/chromium histidinate resulted in a significant decrease in free fatty acid levels in rats fed a normal or high fat diet. FIGS. 5A and 5B. Surprisingly, the treatment group that received chromium picolinate/chromium histidinate (in the same total amount of elemental chromium as provided by chromium picolinate or chromium histidinate alone) had significantly lower free fatty acid levels than the treatment groups that received chromium supplementation in the form of chromium as chromium picolinate or chromium histidinate alone. FIG. 5B. The synergistic effect of the combination could not have been predicted.

Example 3

Combination Chromium Supplementation to Achieve Sustained Release of Chromium

Combination supplementation with a fast-acting chromium complex and a slow-acting chromium complex results in a sustained release of chromium over a period of time. More specifically, the combination chromium supplementation is useful in achieving prolonged, sustained chromium absorption to an individual in need thereof. Chromium supplementation has many therapeutic indications. For example, chromium has been associated with the improvement of glucose metabolism, mitigation of insulin resistance, improvement of symptoms associated with hyperglycemia, improvement of lipid profiles, promotion of lean body mass, and the reduction of obesity.

One of the surprising aspects of the present invention is the discovery that the combination chromium supplementation with a hydrophilic chromium complex and lipophilic chromium complex results in a greater than additive effect in ameliorating some of the diseases, conditions, and associated symptoms disclosed above. Without being bound to a particular theory, it is believed that the synergistic effects observed with combination chromium therapy can be attributed to the achievement of rapid chromium absorption via the hydrophilic chromium complex supplementation and sustained, long-term absorption via the lipophilic chromium complex supplementation. By combining a fast-acting chromium complex with a slow-acting chromium complex, prolonged, sustained absorption of chromium by an individual in need thereof is accomplished.

An individual presenting with poor glucose metabolism is identified (e.g. either self-identified or identified by other means). The individual is administered a nutritional supplement comprising an effective dose of chromium histidinate and an effective dose of chromium picolinate. Glucose metabolism is monitored and an improvement in glucose metabolism is observed.

An individual with high LDL cholesterol and low HDL cholesterol is identified (e.g. either self-identified or identified by other means). The individual is administered an effective dose of chromium acetate and an effective dose of chromium picolinate. An improvement of the individual's lipid profile is observed. LDL cholesterol is lowered and HDL cholesterol is raised.

An individual with insulin resistance is identified (e.g. either self-identified or identified by other means). The individual is administered a dietary beverage comprising an effective dose of chromium histidinate and an effective dose of chromium picolinate. The individual's response to insulin is monitored. The supplementation with chromium histidinate and chromium picolinate results in an improvement in insulin sensitivity.

The methods, compositions, and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. Accordingly, it will be apparent to one skilled in the art that varying substitutions and modifications can be made to the invention disclosed herein without departing from the scope and spirit of the invention.

As used in the claims below and throughout this disclosure, by the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Numerous literature and patent references have been cited in the present patent application. Each and every reference that is cited in this patent application is incorporated by reference herein in its entirety.

What is claimed is:

1. A composition for administering chromium over a period of time, the composition comprising a synergistic ratio of chromium provided in the form of a hydrophilic chromium complex to chromium provided in the form of a lipophilic chromium complex,
    wherein the hydrophilic chromium complex is selected from the group consisting of chromium acetate, chromium chloride, chromium histidinate and chromium nicotinate, the lipophilic chromium complex is chromium picolinate, and the synergistic ratio is between about 1:2 and 2:1.

2. A composition for administering chromium over a period of time, the composition consisting essentially of chromium histidinate and chromium picolinate.

3. The composition of claim 1, wherein said hydrophilic chromium complex is chromium histidinate.

4. The composition of claim 1, further comprising a nutritionally acceptable carrier.

5. A composition for providing bioavailable chromium, the composition comprising chromium histidinate and chromium picolinate, wherein the ratio of chromium histidinate to chromium picolinate is between about 1:2 and 2:1.

* * * * *